United States Patent
Mizobuchi et al.

(10) Patent No.: US 9,895,276 B2
(45) Date of Patent: Feb. 20, 2018

(54) UNDERPANTS-TYPE DISPOSABLE DIAPER HAVING SIDE SEAL SECTIONS WITH WELDED REGIONS OF DIFFERING DENSITIES

(71) Applicant: DAIO PAPER CORPORATION, Ehime (JP)

(72) Inventors: Keita Mizobuchi, Ehime (JP); Nobuyuki Okada, Ehime (JP); Ryoichi Ochi, Ehime (JP); Terumasa Kamioka, Ehime (JP)

(73) Assignee: DAIO PAPER CORPORATION, Ehime (JP)

( * ) Notice: Subject to any disclaimer, the term of this patent is extended or adjusted under 35 U.S.C. 154(b) by 862 days.

(21) Appl. No.: 14/372,973

(22) PCT Filed: Jan. 17, 2013

(86) PCT No.: PCT/JP2013/050731
§ 371 (c)(1),
(2) Date: Jul. 17, 2014

(87) PCT Pub. No.: WO2013/108808
PCT Pub. Date: Jul. 25, 2013

(65) Prior Publication Data
US 2014/0378925 A1    Dec. 25, 2014

(30) Foreign Application Priority Data
Jan. 20, 2012  (JP) .................................. 2012-009723

(51) Int. Cl.
*A61F 13/15*    (2006.01)
*A61F 13/20*    (2006.01)
(Continued)

(52) U.S. Cl.
CPC .......... *A61F 13/565* (2013.01); *A61F 13/496* (2013.01); *A61F 13/4963* (2013.01);
(Continued)

(58) Field of Classification Search
CPC .................................................. A61F 13/4963
See application file for complete search history.

(56) References Cited

U.S. PATENT DOCUMENTS 5,685,874 A     11/1997   Buell et al.
2008/0140038 A1   6/2008   Sasayama et al.
(Continued)

FOREIGN PATENT DOCUMENTS

EP    0 657 153 A2    6/1995
EP    2 347 744 A1    7/2011
(Continued)

*Primary Examiner* — Michele M Kidwell
(74) *Attorney, Agent, or Firm* — Muncy, Geissler, Olds & Lowe, P.C.

(57) ABSTRACT

In a dot pattern, both sufficient strength during the use of a diaper and the ease of tearing can be achieved, while inhibiting sticking of fiber waste of a non-woven fabric in the sealing device. The problems can be solved by the underpants-type disposable diaper characterized by a side seal section 13 is formed in a dot pattern in which a plurality of rows of dot-shaped welded parts 13s, 13b, disposed with intervals in a vertical direction, are disposed in a transverse direction, and non-welded parts 13n, disposed all over in the transverse direction, are disposed on both sides of each welded part 13s, 13b, in the vertical direction; the side seal section 13 has at least partly in the vertical direction a non-densely welded region LD and a densely welded region HD; and each welded part 13b in the densely welded region HD is larger in area than each welded part 13s in the non-densely welded region LD.

5 Claims, 12 Drawing Sheets

(51) Int. Cl.
*A61F 13/56* (2006.01)
*A61F 13/496* (2006.01)
*A61F 13/51* (2006.01)
*B29L 31/48* (2006.01)
*B29C 65/08* (2006.01)
*B29C 65/00* (2006.01)

(52) U.S. Cl.
CPC .... *A61F 13/51* (2013.01); *A61F 2013/51014* (2013.01); *A61F 2013/51026* (2013.01); *A61F 2013/5694* (2013.01); *B29C 65/08* (2013.01); *B29C 66/1122* (2013.01); *B29C 66/21* (2013.01); *B29C 66/232* (2013.01); *B29C 66/431* (2013.01); *B29C 66/7294* (2013.01); *B29L 2031/4878* (2013.01)

(56) References Cited

U.S. PATENT DOCUMENTS

2011/0125124 A1* 5/2011 La Von ............... A61F 13/496
604/385.23
2012/0278975 A1* 11/2012 Yamashita ........ A61F 13/49466
2/400
2012/0284904 A1* 11/2012 Otsubo .................. B29C 65/08
2/400

FOREIGN PATENT DOCUMENTS

| | | |
|---|---|---|
| EP | 2 412 354 A1 | 2/2012 |
| JP | H10137287 A | 5/1998 |
| JP | H11140706 A | 5/1999 |
| JP | 2000316898 A | 11/2000 |
| JP | 2002272785 A | 9/2002 |
| JP | 2002369842 A | 12/2002 |
| JP | 2003024381 A1 | 1/2003 |
| JP | 2003038573 A | 2/2003 |
| JP | 200314494 A1 | 5/2003 |
| JP | 2008136651 A | 6/2008 |
| JP | 2010115424 A | 5/2010 |
| JP | 2010119577 A | 6/2010 |
| WO | WO 2010/110203 A1 | 9/2010 |

* cited by examiner

UNDERPANTS-TYPE DISPOSABLE DIAPER HAVING SIDE SEAL SECTIONS WITH WELDED REGIONS OF DIFFERING DENSITIES

TECHNICAL FIELD

The present invention relates an underpants-type disposable diaper.

BACKGROUND ART

In many cases, an underpants-type disposable diaper is formed of a liquid-permeable surface sheet, a back side sheet, and an absorber interposed between them, including gathers for areas around legs at both sides thereof, an inner body formed so as to cover from a back side through a crotch portion to a ventral side, and an outer sheet bonded to an outer surface of the inner body and formed so as to cover the abdomen portion and the crotch portion, with an underpants-type structure in which a back body part and a front body part of the outer sheet are each joined together on both sides by heat sealing or ultrasonic sealing to form side seal sections, whereby a waist opening and leg openings are previously formed.

Such an underpants-type disposable diaper is unclothed after excretion or the like by tearing off the back body part and the front body part from each other at the side seal sections thereof so as to be removed from the body. As a result, the side seal section is required to provide not only a seal strength enough not to be broken during the use of the diaper but also ease of tearing off after the use of the diaper. Various techniques, accordingly, have been conventionally suggested (see, for example, Patent Documents 1 to 10). For example, techniques described in Patent Documents 1 and 2 suggest seal patterns designed in view of the number of material sheets in the side seal sections.

Especially, a dot pattern in which dot-shaped welded parts are alternately arranged in a serpentine pattern, as shown in FIG. 6 of Patent Document 1 or 2 or Patent Document 5, has an advantage, i.e., the tearing is more easily performed in the dot pattern than a horizontal stripe pattern in which welded straight lines each disposed along in a transverse direction (in the form of a rectangle whose long sides are disposed in a transverse direction, and the like) are arranged in a vertical direction, as shown in Patent Document 4.

CITATION LIST

Patent Documents

Patent Document 1: JP 2010-115424 A
Patent Document 2: JP 2010-119577 A
Patent Document 3: JP 2000-316898 A
Patent Document 4: JP 2003-38573 A
Patent Document 5: JP 2002-369842 A
Patent Document 6: JP 10-137287 A
Patent Document 7: JP 2003-24381 A
Patent Document 8: JP 2002-272785 A
Patent Document 9: JP 2003-144494 A
Patent Document 10: JP 11-140706 A

SUMMARY OF INVENTION

Technical Problem

In application of the conventional patterns, however, it is sometimes difficult to achieve the sufficient strength during the use of the diaper and the ease of tearing. For example, if there is an area where only non-woven fabrics of polypropylene (hereinafter which may sometimes be referred to as "PP") or a copolymer thereof are laminated in a section such as side seal section of a waist edge part, the seal strength of this area is several times as much as that of the rest. Nevertheless, if such area is made to be easily torn in application of the conventional pattern, the rest inevitably turns to be broken too easily during the use of the diaper.

Alternatively, in that case, it can be assumed that a dot pattern is employed where welded parts are partly increased. Only by increasing partly the welded parts, however, fiber waste of the non-woven fabric tends to stick in gaps between protrusions, which are disposed for forming the welded parts in a sealing device (for example, it is necessary to clean up the fiber waste four times as often as an ordinary horizontal stripe pattern), and additionally, it becomes difficult to remove the fiver waste stuck.

The main object of the present invention is to achieve, in the dot pattern, both the sufficient strength during the use of the diaper and the ease of tearing, while inhibiting sticking of the fiber waste of the non-woven fabric in the sealing device.

Solution to Problem

The present invention solving the problems described above is as follows:

<Invention According to Claim 1>

An underpants-type disposable diaper, in which a front body part and a back body part are each weld-jointed together on both sides to form side seal sections, thereby forming a waist opening and a right-left pair of leg openings, characterized by:

at least an outer surface of the side seal section is formed of a non-woven fabric; the side seal section is formed in a dot pattern in which a plurality of rows of dot-shaped welded parts, disposed with intervals in a vertical direction, are disposed in a transverse direction, and non-welded parts, disposed all over in the transverse direction, are disposed on both sides of each welded part in the vertical direction;

the side seal section is set to have a non-densely welded region at least partly in the vertical direction and a densely welded region at least partly in the vertical direction; and each welded part in the densely welded region is at least partly larger in area than each welded part in the non-densely welded region.

Effect and Operation

In general, in order to tear off the side seal sections of the underpants-type disposable diaper, hands are put into the front body part side and the back body part side from the waist opening, the front body part side and the back body part side of the side seal sections are grabbed by the hands, and the front body part and the back body part are pulled so as to separate from each other, whereby welded parts forming the side seal sections are torn sequentially from the waist side. In this occasion, the seal strength depends on the total area of the welded parts, which are removed at once, and thus the seal strength is high in the densely welded region while the seal strength is weak in the non-densely welded region. Both the sufficient strength during the use of the diaper and the ease of tearing can be achieved, accordingly, by providing the densely welded region and the non-densely welded region at appropriate sites depending on the site in the side seal section.

In particular, the side seal sections in the present invention are formed in a dot pattern having the non-welded parts, disposed all over in the transverse direction, on both sides of each welded part in the vertical direction, which inhibits the fiber waste of the non-woven fabric from sticking in gaps between protrusions for forming the welded parts in a sealing device, and the stuck fiber waste can be easily removed. In manufacturing of the underpants-type disposable diaper, the side seal sections are formed while the diaper is moved in the transverse direction; as a result, even if the fiber waste is generated, it is discharged through depression grooves (between the protrusions for forming the welded parts) for forming the non-welded parts in the sealing device, which prevents the fiber waste from accumulating between the protrusions for forming the welded parts. Specifically, the staying time of the fiber waste is substantially the same as that in the conventional general horizontal stripe pattern. Even if the fiber waste has accumulated between the protrusions for forming the welded parts after a long period of time elapses, it can be easily removed only by brushing in a flow direction of the line, because the grooves between the protrusions run continuously in the flow direction of the line.

Furthermore, according to the present invention, the area of the welded part is increased in the densely welded region, which makes it possible to reduce the generation of the fiber waste.

As a result, in the dot pattern, both the sufficient strength during the use of the diaper and the ease of tearing can be achieved, while inhibiting the fiber waste of the non-woven fabric from sticking in the sealing device.

<Invention According to Claim 2>

The underpants-type disposable diaper according to claim 1, wherein the side seal section has a polypropylene region where only non-woven fabrics of polypropylene or a copolymer thereof are laminated, and the non-densely welded region is formed in the polypropylene region.

Effect and Operation

The non-woven fabric of the polypropylene or the copolymer thereof is a preferable material, because it is easily stretchable, and a soft texture can be obtained therefrom. When such a polypropylene region is disposed in the side seal section, however, the seal strength of this area is several times as much as that of the rest, and it is difficult to apply a force thereto because the material is easily stretched, as described above. Accordingly, in the present invention, it is desirable to apply the non-densely welded region in such a polypropylene region.

<Invention According to Claim 3>

The underpants-type disposable diaper according to claim 2, wherein in the side seal section, a waist edge part is set to be the polypropylene region, and leg opening-side portion with respect to the waist edge part is totally set to be a non-polypropylene region, which is not the polypropylene region, and the non-densely welded region is set to be provided from the polypropylene region into the non-polypropylene region, and the densely welded region is set to be provided on the leg opening-side with respect to the non-densely welded region.

Effect and Operation

As for the ease of tearing of the side seal sections, ease of peeling at the start of tearing is very important. If the diaper had the polypropylene region at the waist edge part, the seal strength would increase so as to make the user feel difficult to tear off the diaper. Accordingly, in the present invention, it is desirable to apply the non-densely welded region in the polypropylene region in the waist edge part.

In the side seal section, when the leg opening-side portion with respect to the waist edge part is totally set to be the non-polypropylene region, it is desirable that the non-polypropylene region is set to be the densely welded region in order to reduce the variation of the seal strength. Under such condition, when it is intended that a boundary between the non-densely welded region and the densely welded region is agreed with a boundary between the polypropylene region and the non-polypropylene region, the densely welded region might enter the polypropylene region due to manufacturing error, which could likely lead to generation of locally high seal strength. As described before, accordingly, it is desirable that the boundary between the both regions is disposed inside the non-polypropylene region, in particular, on the edge thereof at the polypropylene region-side (in a first region in the embodiment shown by the drawings).

<Invention According to Claim 4>

The underpants-type disposable diaper according to any one of claims 1 to 3, wherein each welded part in the side seal section has the shape of a circle having a diameter of 0.7 to 2.0 mm, each welded part in the densely welded region has an area being 1.5 to 3.5 times as large as each welded part in the non-densely welded region, the number of rows of the welded parts arranged in the non-densely welded region is two, the number of rows of the welded parts arranged in the densely welded region is more than the number of the rows in the non-densely welded region, the non-welded part in the non-densely welded region has a length of 0.05 to 2.0 mm in the vertical direction, and the non-welded part in the densely welded region has a length of 0.05 to 3.0 mm in the vertical direction.

Effect and Operation

In the present invention, the dimension and configuration of the dot pattern may be appropriately decided, but the ranges described above are preferable for the diaper used for babies.

<Invention According to Claim 5>

The underpants-type disposable diaper according to any one of claims 1 to 4, wherein weld-jointing is performed by ultrasonic sealing.

Effect and Operation

The ultrasonic sealing hardly thermally affects a surrounding around the welded part, compared to the heat sealing, and the finished material in the side seal section is easily stretchable and is soft. However, the ultrasonic sealing makes the user feel more difficult to tear off the diaper, when compared to the heat sealing in terms of the same seal pattern, because of the easy stretchability of the material. The present invention is preferable when the ultrasonic sealing is adopted.

Advantageous Effects of Invention

As described above, in the dot pattern according to the present invention, advantages are provided in which both the sufficient strength during the use of the diaper and the ease of tearing can be achieved, while inhibiting sticking of the fiber waste of the non-woven fabric in the sealing device.

DESCRIPTION OF EMBODIMENTS

Embodiments of the present invention will be described below in detail with reference to the attached drawings.

FIGS. 1 to 8 show one embodiment of an underpants-type disposable diaper 100. The underpants-type disposable diaper 100 is formed of an outer sheet 12, which is an outer surface (back side) of a product, and an inner body 200, which is bonded to an inner surface of the outer sheet 12. Reference alphabet Y denotes a full length of the diaper (a length in the vertical direction from an edge of a waist opening WO of a front body part F to an edge of the waist opening WO of a back body part B) in an open state; and reference alphabet X denotes a full width of the diaper in an open state.

The inner body 200 is a member absorbing and retaining excreta such as urine and the outer sheet 12 is a member for putting the diaper to a wearer. Dots in cross-section views denote joint points at which structural members are joined to each other, and are formed by mat coating, bead coating, curtain coating, cermet coating, or spiral coating with a hot-melt adhesive, or the like. The term "front-back direction" refers to a direction that links a ventral side (front side) to a back side (rear side); the term "width direction" refers to a direction (right-left direction) orthogonal to the front-back direction; and the term "up-down direction" refers to a direction that becomes orthogonal to an abdomen direction when the diaper 100 is used, that is, when the diaper 100 is folded in two such that a front part and a back part are overlapped at both sides, in other words, a direction that links a waist opening WO to a crotch portion.

(Inner Body)

Figure 1:
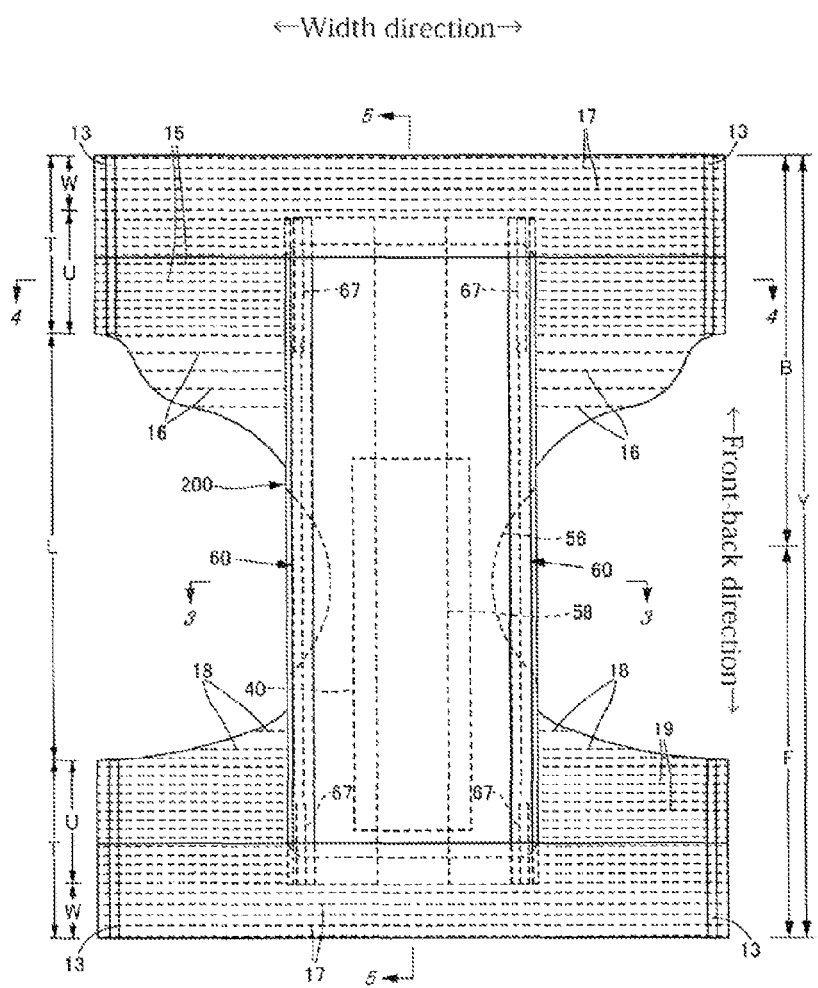
FIG. 1 is a plan view showing an inner surface of an underpants-type disposable diaper in an open state of a diaper.
Figure 2:
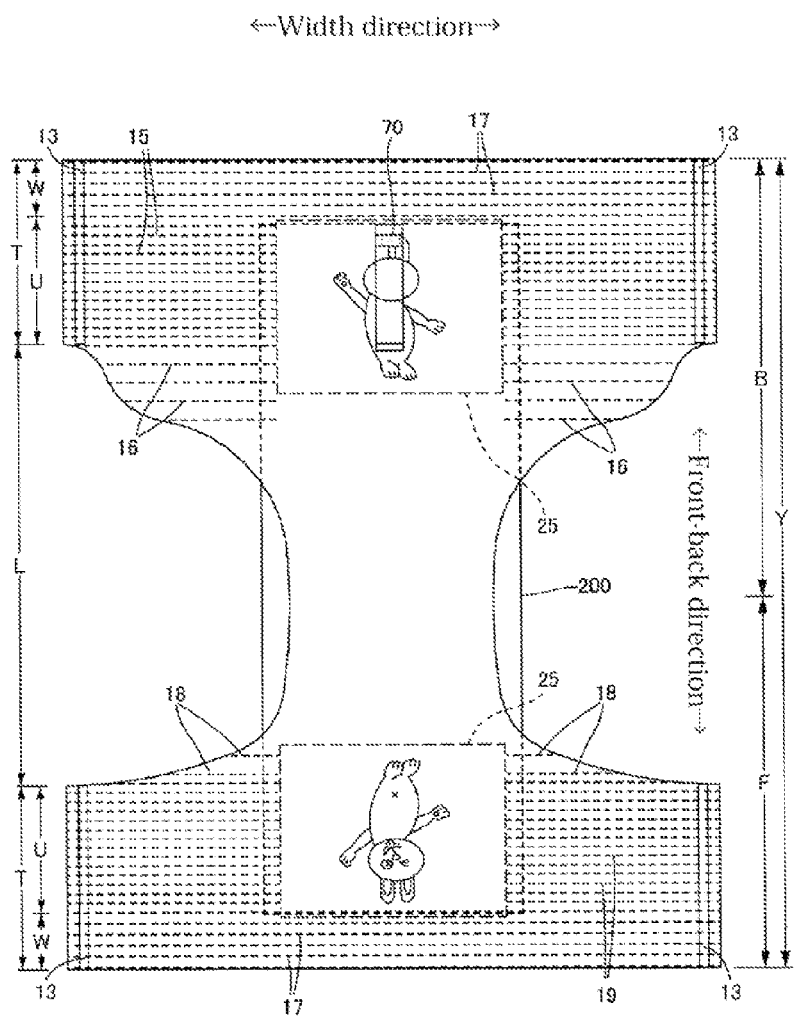
FIG. 2 is a plan view showing an outer surface of an underpants-type disposable diaper in an open state of a diaper.
Figure 3:
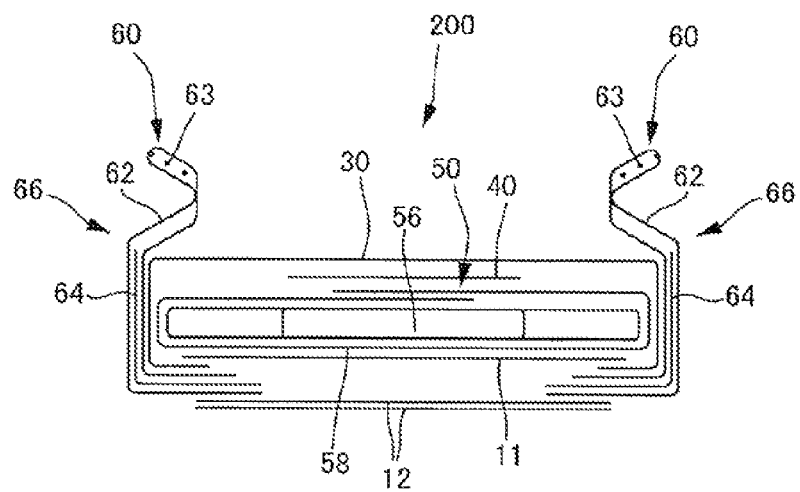
FIG. 3 is a cross-section view of FIG. 1 taken along line 3-3.
Figure 4:
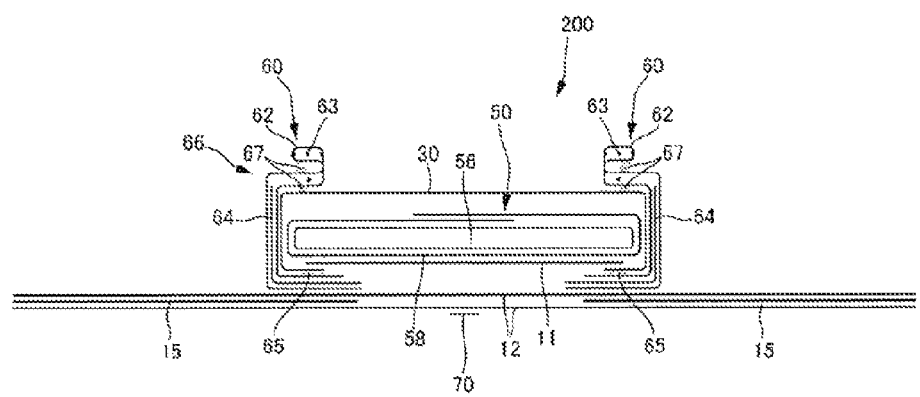
FIG. 4 is a cross-section view of FIG. 1 taken along line 4-4.
Figure 5:
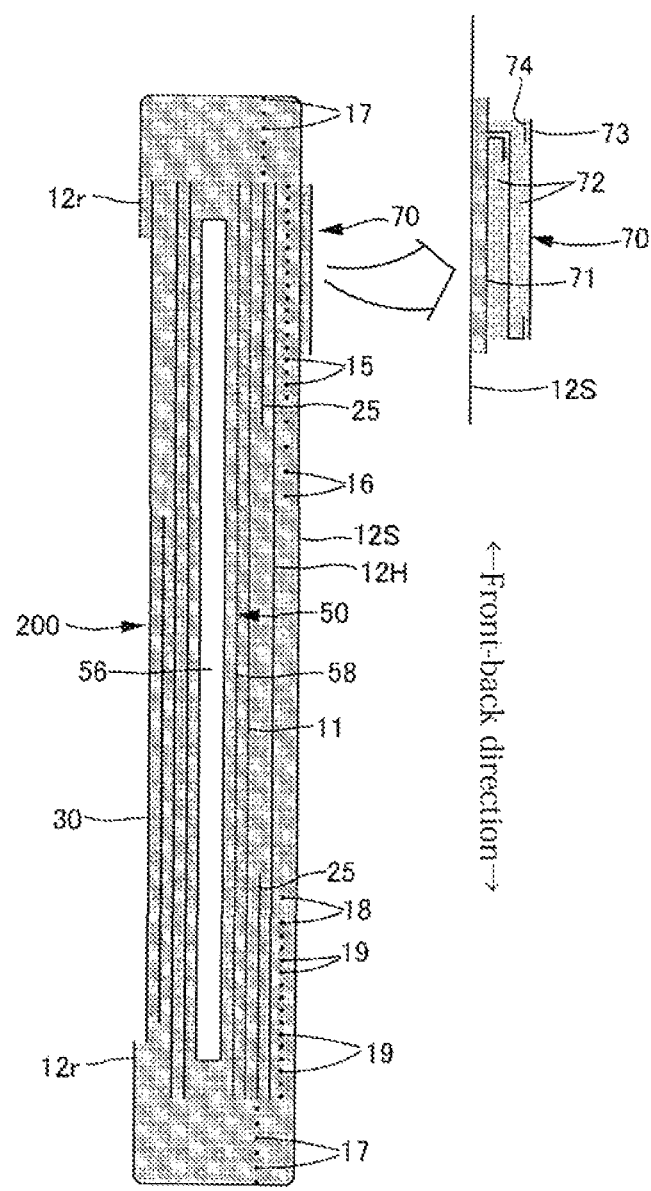
FIG. 5 is a cross-section view of FIG. 1 taken along line 5-5.

The inner body 200 may has any shape, and is a rectangle in the embodiment shown by the drawings. The inner body 200 includes, as shown in FIGS. 3 to 5, a surface sheet 30, which is on a body side, a liquid-impermeable back sheet 11, and an absorbent element 50, which is interposed between them; and is a main body part, which carries on an absorption function. Reference number 40 denotes an interlayer sheet (second sheet), which is provided between the surface sheet 30 and the absorbent element 50 to move promptly liquid passing through the surface sheet 30 to the absorbent element 50; and reference number 60 donates three dimensional gather 60 standing on the body side and the three dimensional gathers 60 are provided on both sides of the inner body 200 to prevent leakage of excreta to both sides of the inner body 200.

(Surface Sheet)

The surface sheet 30 has a liquid-permeability, and each example thereof may include a non-woven fabric with or without pores, a porous plastic sheet, and the like. Such a non-woven fabric has no particular limitation in raw fibers therefor. For example, the raw fibers may be any of synthetic fibers based on olefin such as polyethylene or polypropylene, polyester, polyamide or the like, recycled fibers such as rayon or cupra, natural fibers such as cotton or the like, mixed or composite fibers of two or more of the foregoing fibers. Further, the non-woven fabric may be produced by any processing method. As the method, for example, there are conventional methods such as spun lace method, spun bonded method, thermal bonded method, melt-blown method, needle punched method, air-through method, point bonded method, and the like. If the softness or the drape property is desired, the spun bonding method and the spun lace method are preferable, and if the bulkiness and the softness are desired, the air-through method, the point bonding method, and the thermal bonding method are preferable.

The surface sheet 30 may be formed of one sheet, or may be formed of a laminated sheet obtained by bonding two or more sheets to each other. Similarly, the surface sheet 30 may be formed of one sheet or two or more sheets with respect to a plane direction.

When the three dimensional gathers 60 are provided, it is preferable that both sides of the surface sheet 30 are extended so as to wrap themselves around the absorbent element 50 to the under surface thereof through between the liquid-impermeable back sheet 11 and the three dimensional gathers 60, and they are joined to the liquid-impermeable back sheet 11 and the three dimensional gathers 60 with the hot-melt adhesive to prevent penetration of liquid.

(Interlayer Sheet)

To rapidly move a liquid having permeated through the surface sheet 30 to the absorber, an interlayer sheet (also called "second sheet") 40 may be provided, which is higher in liquid permeability rate than the surface sheet 30. The interlayer sheet 40 allows a liquid to move quickly to the absorber to thereby enhance an absorption performance of the absorber, and prevents a "passing back" phenomenon in which a liquid flows back from the absorber to thereby keep the surface sheet 30 in a dry condition. The interlayer sheet 40 may be omitted.

The interlayer sheet 40 may use the same material as that for the top sheet 30, or may use a spun lace non-woven fabric, a spun bond non-woven fabric, an SMS non-woven fabric, a pulp non-woven fabric, a mixed sheet of pulp and rayon, point-bonded or crepe paper, for example. In particular, an air-through non-woven fabric has bulkiness and thus preferred. Such an air-through non-woven fabric uses preferably mixed fibers of a core-sheath structure. In this case, material resin for the core may be polypropylene (PP) but is preferably high-stiffness polyester (PET). A basis weight of the non-woven fabric is preferably 20 to 80 g/m$^2$, more preferably 25 to 60 g/m$^2$. A fineness of material fibers for the non-woven fabric is preferably 2.2 to 10 dtex. To make the non-woven fabric high-bulk, some or all of the material fibers use preferably mixed fibers with off-center cores or hollow centers, or mixed fibers with off-center cores and hollow centers.

Although, in the illustrated embodiment, the interlayer sheet 40 is made shorter in width than the absorber 56 and is centered with respect to the absorber 56, the interlayer sheet 40 may also be provided across an entire width of the absorber 56. A length of the interlayer sheet 40 in the longitudinal direction may be the same as that of the absorber 56, or may be in a shorter range centered in an area for receiving a liquid.

(Liquid-Impermeable Back Sheet)

There is no particular limitation on a material for the liquid impervious sheet 11. For example, the material may be any of a plastic film of olefin resins such as polyethylene and polypropylene, a laminated non-woven fabric in which a plastic film is provided on a non-woven fabric, a laminated sheet in which a non-woven fabric is laminated on a plastic film and the like. Additionally, for the liquid impervious sheet 11, it is preferable to use a liquid impervious and moisture pervious material that has been favorably used in recent years from the viewpoint of prevention of stuffiness. Such a liquid impervious and moisture pervious plastic film may be a microporous plastic film obtained by melting and kneading an inorganic filling agent into an olefin resin such as polyethylene or polypropylene to thereby form a sheet and then extending the sheet in a uniaxial or biaxial direction, for example. Further, the liquid impervious sheet 11 may use a sheet that is given liquid imperviousness without the use of a water-proof film, by using a non-woven fabric of micro denier fibers, applying heat or pressure to make gaps in fibers smaller with enhanced leakage resistance, coating with high water-absorption resin or hydrophobic resin, or applying a water repellent agent.

The liquid impervious sheet 11 preferably is extended so as to wrap itself around the both sides of the absorbent element 50 to the both side portions of the surface sheet 30 in the absorbent element 50, thereby to enhance a leakage preventing property. An appropriate width of the extended portion is about 5 to 20 mm on both of the right and left sides.

Further, the liquid impervious sheet 11 may have inside thereof, particularly on the side of the absorber 56, an excretion indicator that changes in color when absorbing a liquid.

(Three Dimensional Gather)

The three dimensional gathers 60 are band-like members that extend in the entire front-back direction along the both sides of the inner body 200 and provided to block urine or loose stool moving laterally over the surface sheet 30 and to prevent lateral leakage. Each of the three dimensional gathers 60 in this embodiment is diagonally from the side portion of the inner body 200, a root section thereof is diagonally erected toward the central portion of the inner body in the width direction, and a leading end section thereof is diagonally erected outward in the width direction from the center line thereof.

More specifically, the three dimensional gather 60 is configured in such a manner that a band-like barrier sheet 62 being the same in length as the inner body 200 in the front-back direction, is folded back and doubled in the width direction, and a plurality of elongated stretchable elastic members 63 is fixed in an extended state in the longitudinal direction at intervals therebetween in the width direction. In the three dimensional gather 60, the base part, which is opposite to the leading edge (, that is an end part, which is opposite to the folded back section of the sheet in the width direction) is designated as an attaching part 65 that is fixed on the underside surface of the inner body 200 and the rest thereof is designated as a projecting part 66 (at the folded back section-side). The projecting part 66 consists of the root section, which is erected toward the central portion of the inner body in the width direction, and the leading end section, which is folded back from the leading edge of the root section outward in the width direction. This embodiment has the surface contact-type three dimensional gather, and a line contact-type three dimensional gather (not shown), which is not folded outward in the width direction, may also be adopted. In the projecting part 66, both end portions thereof in the front-back direction are fixed in a fallen state to the surface of the side portion of the surface sheet 30 with the use of a hot-melt adhesive or heat-sealing so as to be front and back fixed portions 67, whereas, an intermediate portion in the front-back direction, which is located between the fixed portions, is designated as a free portion, which is not fixed, and the elongated stretchable elastic member 63 along the front-back direction is fixed to this free portion in a stretched state.

The barrier sheet 62 may use favorably a soft non-woven fabric with excellent uniformity and concealment properties such as spun-bonded non-woven fabrics (SS, SSS, and the like), SMS non-woven fabrics (SMS, SSMMS, and the like), or melt-blown non-woven fabrics, which are made water-repellent as required using silicon or the like. A basis weight of fibers in the fabric is preferably about 10 to 30 g/m$^2$. The elongated stretchable elastic members 63 may use rubber threads or the like. If spandex rubber threads are used, a fineness thereof is preferably 470 to 1,240 dtex, more preferably 620 to 940 dtex. The spandex rubber threads are preferably fixed at an extension ratio of preferably 150 to 350%, more preferably 200 to 300%. The term "elongation rate" refers to a value to a natural length which is defined as 100%. In addition, although not shown, a water-proof film may be interposed in the two-fold barrier sheet.

The number of the elongated stretchable elastic members 63 is preferably 2 to 6, more preferably 3 to 5, at each of free portions of the three dimensional gather 60. The interval 60d therebetween is appropriately set between 3 to 10 mm. In such an arrangement, the three dimensional gather 60 are likely to contact the skin of a wearer in areas with the elongated resilient stretchable members 63. The three dimensional gather 60 may also have the elongated stretchable elastic members 63 at the root-side as well as the leading edge-side.

The attaching part 65 of the three dimensional gather 60 may be fixed to appropriate members of the inner body 200, such as the surface sheet 30, the liquid-impermeable back sheet 11, and the absorbent element 50.

In the thus configured three dimensional gathers 60, the contraction forces of the elongated stretchable elastic members 63 act so as to bring the both front and back ends closer to each other. In the projecting part 66, the both end portions in the front-back direction are fixed so as not to be erected, on the other hand, the portion located between them is set to be free portion. As a result, as shown in FIG. 3, only the free portion is erected so that it is brought into contact with the body side. In particular, since the attaching part 65 is located on the underside surface of the inner body 200, the three dimensional gather 60 is erected so as to open outward in the width direction in the crotch portion and the vicinity thereof, and the three dimensional gather 60 is brought into surface contact with an area around a leg, resulting in improved fitting property.

Figure 7:
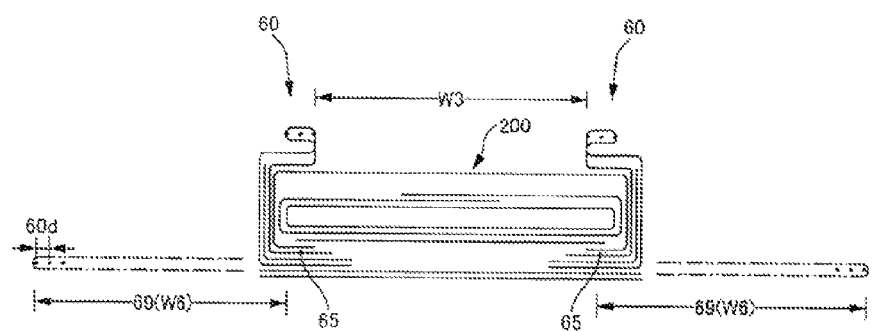
FIG. 7 is a cross-section view showing only a major part of an underpants-type disposable diaper.

The dimensions of the three dimensional gather 60 can be appropriately decided, and in a case of a disposable diaper for babies, as shown in FIG. 7, the height (a length of the projecting part 66 in the width direction in an open state) W6 of the erected part of the three dimensional gather 60 is preferably from 15 to 60 mm, more preferably from 20 to 40 mm. The clearance W3 between folding lines located at the innermost positions when the three dimensional gather 60 is folded so as to be parallel to a surface of a top sheet 30 is preferably from 60 to 190 mm, more preferably from 70 to 140 mm.

The three dimensional gathers may be provided doubly (two rows) in the inner body 200 at the right and left side portions thereof respectively, unlike the embodiment shown in the drawings.

(Absorbent Element)

The absorbent element 50 has an absorber 56 and a wrapping sheet 58 which wraps the whole of the absorber 56. The wrapping sheet 58 may be omitted.

(Absorber)

The absorber 56 may be made of an assembly of fibers. As the assembly of fibers, in addition to an accumulation of short fibers of fluff pulp or synthetic fiber or the like, an assembly of filaments may be used also, which are obtained by opening as desired a tow (fiber bundle) of synthetic fibers such as cellulose acetate. The fiber basis weight may be, for example, from about 100 to 300 g/m$^2$ for accumulating the fluff pulp or short fibers, and from about 30 to 120 g/m$^2$ for the assembly of filament. The fineness of the synthetic fiber is, for example, from 1 to 16 dtex, preferably from 1 to 10 dtex, more preferably from 1 to 5 dtex. In the case of the assembly of filament, the filament may be a non-crimped fiber, but a crimped fiber is preferable. The number of crimps of the crimpled fiber may be, for example, from about 5 to 75 crimps, preferably from about 10 to 50 crimps, more preferably from about 15 to 50 per inch. The uniformly crimped fibers are often used. It is preferable that high absorbent polymer particles are dispersed and held in the absorber 56.

Figure 6:
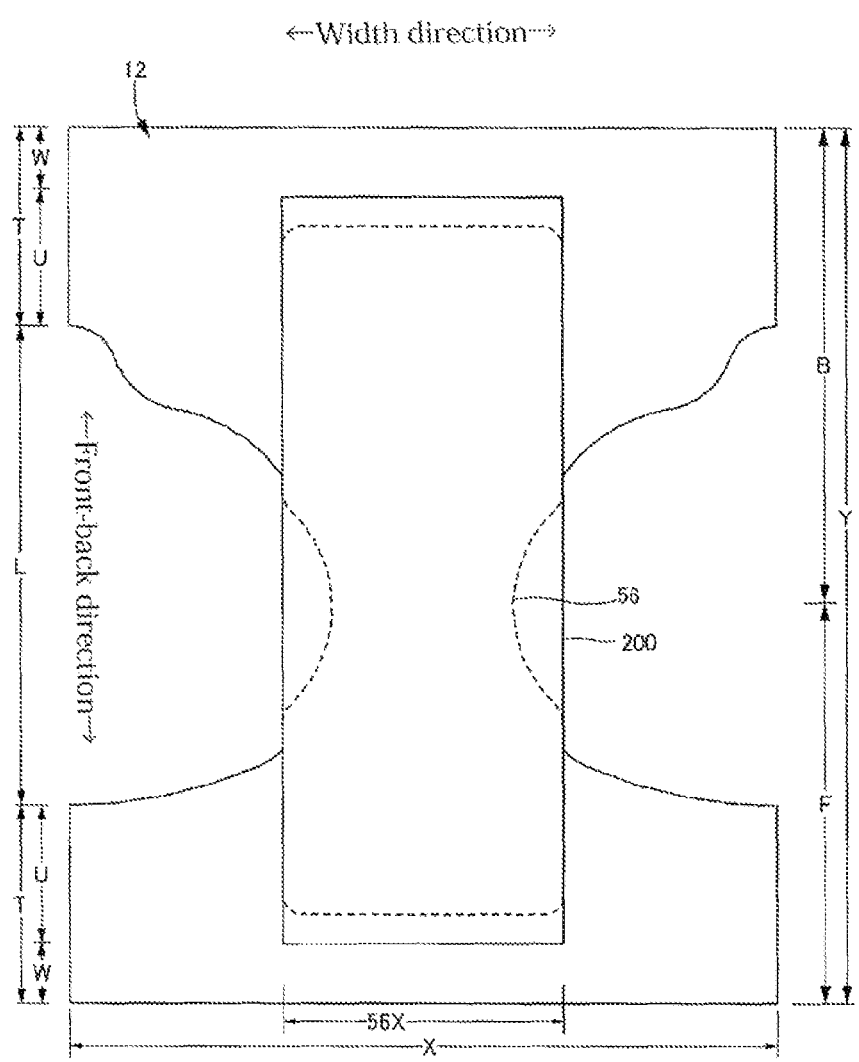
FIG. 6 is a plan view showing only a major part of an underpants-type disposable diaper in an open state of a diaper.

The absorber 56 may be in the shape of a rectangle. As shown in FIG. 6, however, in order to improve fitting property of the diaper to the areas around legs at the absorber 56 itself and at the three dimensional gathers 60, it is preferable that the absorber has the shape of hourglass comprised of a front end part, a back end part, and a part, which is disposed between them and which has a width narrower than those of them.

The dimensions of the absorber may be appropriately decided, and it is preferable that the absorber extends, in the front-back direction and the width direction, to a peripheral edge portion or the vicinity thereof of the inner body. Reference number 56X denotes a width of the absorber 56.

(High Absorbent Polymer Particle)

High absorbent polymer particles may be contained in the absorber 56 as a whole or in a part. The high absorbent polymer particle includes a "powder" in addition to a "particle." As the high absorbent polymer particle 54, those used in this kind of absorbent articles can be used as they are. It is preferable to use particles, such that 30% by weight or less of particles remain on a 500 µm standard sieve (JIS Z 8801-1:2006) after the particles are subjected to sieving (5 minute shaking) with the standard sieve, or such that 60% by weight or more of particles remain on a 180 µm standard sieve (JIS Z 8801-1:2006) after the particles are subjected to sieving (5 minute shaking) with the standard sieve.

Any material of the high absorbent polymer particle can be used without particular limitations, and preferable material is 40 g/g or more in capacity of water absorption (JIS K 7223-1996 "Testing Method for Water Absorption Capacity of Super Absorbent Polymers"). The high-absorbent polymer particles may be based on starch, cellulose or synthetic polymer, and may use starch-acrylic acid (salt) graft copolymer, saponified product of starch-acrylonitrile copolymer, cross-linked sodium carboxymethyl cellulose, acrylic acid (salt) polymer, or the like. A shape of the high absorbent polymer particle is preferably a commonly used particulate shape, and may also be any other shape The high absorbent polymer particles preferably deliver a water absorption speed of 40 seconds or less. If the water absorption speed exceeds 40 seconds, a passing back phenomenon becomes prone to occur, where a liquid having been supplied to the absorber 56 flows back out of the absorber 56.

The high-absorbent polymer particles are preferably 1,000 Pa or more in gel strength. This prevents effectively a sticky feel after absorption of a liquid even if the absorber 56 is high-bulk.

A basis weight of the high-absorbent polymer particles may be decided as appropriate in accordance with an absorption capacity required for the absorber 56, and may be 50 to 350 g/m$^2$, although it is not always defined so. By setting the basis weight of the polymers at 50 g/m$^2$ or less, it is possible to prevent that weight reduction becomes less effective due to the weight of the polymers when synthetic continuous fibers are used. If the basis weight exceeds 350 g/m$^2$, the high-absorbent polymer particles 54 become saturated in effectiveness and an excessive amount thereof has an unpleasant grainy feel.

If necessary, the high-absorbent polymer particles can be adjusted in dispersing density or dispersing amount in the planar direction of the absorber 56. For example, an amount of dispersion may be made larger at a liquid excreted portion than other portions. With regard to a difference between the sexes, the dispersion density (amount) may be increased at the front side portion for men and increased at the middle portion for women. The absorber 56 may have a local portion (in spot, for example) with no polymer in the planar direction thereof (Wrapping Sheet)

Wrapping sheet 58 may use any of materials such as tissue paper, particularly crepe paper, non-woven fabrics, polyethylene-laminated non-woven fabrics, foraminous sheets, and the like. The sheet desirably does not let high absorbent polymer particles pass through. In using a non-woven fabric instead of crepe paper, a hydrophilic SMS (SMS, SSMMS and the like) non-woven fabric is preferred in particular. A material for such a fabric may be polypropylene, polyethylene/polypropylene, or the like. A basis weight of the fabric is 5 to 40 g/m$^2$, desirably 10 to 30 g/m$^2$ in particular.

Although it may be decided as appropriate how the wrapping sheet 58 wraps, this sheet may wrap the absorber 56 cylindrically so that the wrapping sheet surrounds the top surface, underside surface and both side surfaces thereof, at the same time, the wrapping sheet extends at the front edge part and back edge part thereof beyond the absorber 56 in front back direction, and thus the extended parts are crushed in the front back direction and jointed by jointing means such as a hot-melt adhesive. This is preferable in the terms of ease of manufacturing and prevention of spilling of the high absorbent polymer particles from the absorber in the front back direction.

(Outer Sheet)

Figure 8:
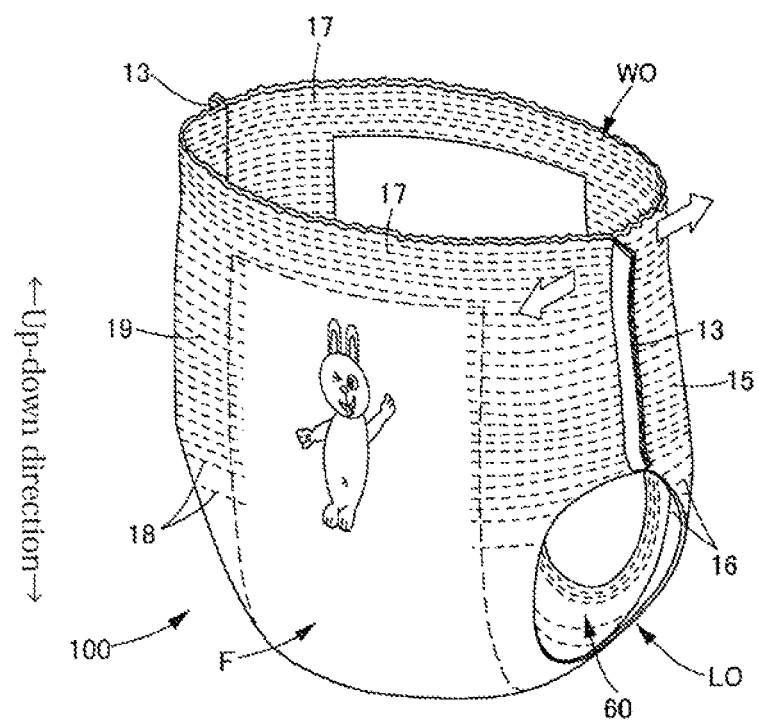
FIG. 8 is a perspective view showing an underpants-type disposable diaper.

The outer sheet 12 has a front body part F corresponding to the front body part of the diaper, which extends from the crotch portion to the ventral side, and a part back body part B corresponding to the back body part of the diaper, which extends from the crotch portion to the back side. The both sides of the front body part F and the both sides of the back body part B are jointed to each other to form the side seal sections 13. As shown in FIG. 8, there are formed the waist opening WO through which the abdomen of a wearer is passed and a right-left pair of leg openings LO through which the legs of the wearer are passed. The term "crotch portion" refers to a center portion in the front-back direction from the waist end edge of the front body part F to the waist end edge of the back body part B in an open state, and the terms "front body part F" and "back body part B" refer to respectively the part on the front side with respect to the crotch portion and the part on the back side with respect to the crotch portion.

The outer sheet 12 has abdomen parts T ranging in the front-back direction from the waist opening WO to the upper end of the leg opening LO, and an intermediate part L ranging in the front-back direction between both ends of the leg opening LO (between the part T in the front-back direction which has the side seal section 13 of the front body part F and the part T in the front-back direction which has the side seal section 13 of the back body part B). The abdomen part T can be conceptually divided into a "waist edge part" W forming the edge part of the waist opening, and an "under waist part" U located below the waist edge part. The lengths thereof in the vertical direction vary depending on the size of a product, and can be appropriately decided. As one example, the length of the waist edge part W can be from 15 to 40 mm, and the length of the under waist part U can be from 65 to 120 mm. On the other hand, the both side edges of the intermediate part L are made narrow along areas around legs of the wearer so that the legs of the wearer pass through there. As a result, the outer sheet 12 is in the shape of almost a sand glass as a whole. The degree of narrowing of the outer sheet 12 may be appropriately decided, and as shown in FIGS. 1 to 8, it is preferable that the narrowest part has a width narrower than that of the inner body 200 in order to obtain an elegant appearance, but the narrowest width may be decided to have a width equal to or wider than that of the inner body 200.

As shown in FIGS. 3 to 5, the outer sheet 12 is formed by bonding two sheet base materials 12S and 12H to each other with an adhesive such as a hot-melt adhesive. The inside sheet base material 12H, which is located on the inside, is extended only to the edge of the waist opening WO, while the outside sheet base material 12S is extended so as to wrap itself around the waist-side edges of the inside sheet base material 12H and fold back to the inside thereof. Thus folded parts 12r are extended so as to cover till the waist-side end parts of the inner body 200.

As the sheet base materials 12S and 12H, any sheet may be used without particular limitations, and as at least the outside sheet base material 12S, a non-woven fabric is used. Such a non-woven fabric has no particular limitation in raw fibers therefor. For example, the raw fibers may be any of synthetic fibers based on olefin such as polyethylene or polypropylene, polyester, polyamide or the like, recycled fibers such as rayon or cupra, natural fibers such as cotton or the like, mixed or composite fibers of two or more of the foregoing fibers. In particular, as the outside sheet base material 12S, the non-woven fabric of the polypropylene or the copolymer thereof (for example, a copolymer in which polyethylene or ethylene is used for copolymerization and hereinafter such a non-woven fabric may sometimes be referred to as a PP-type non-woven fabric) is a preferable material, because a soft texture can be obtained. It is also preferable to use, as the inside sheet base material 12H, a core-sheath fiber (PE/PP) in which polyethylene (PE) is a sheath and polypropylene (PP) is a core component, and a core-sheath fiber (PE/PET) in which polyethylene (PE) is a sheath and polyethylene terephthalate (PET) is a core component.

The non-woven fabric may be produced by any processing method. As the method, for example, there are conventional methods such as spun lace method, spun bonded method, thermal bonded method, melt-blown method, needle punched method, air-through method, point bonded method, and the like. When the non-woven fabric is used, the fineness of the fiber is preferably from about 1.7 to 2.8 dtex, and the base weight is preferably from about 10 to 30 g/m$^2$.

It is also preferable that the total basis weight of the outer sheet 12 (the total basis weight of the outside sheet base material 12S and the inside sheet base material 12H) is from about 20 to 60 g/m$^2$, and the total light transmittance, defined by JIS K 7105, of the outer sheet 12 is 40% or more, particularly 50% or more, in order to recognize visually a design on a printed sheet 25 described below, from the outer surface of the product through the outer sheet 12.

In order to enhance the fitting property to the abdomen, elongated stretchable elastic members 15 to 19 such as rubber thread are provided with predetermined elongation rates between the two sheet base materials 12S and 12H of the outer sheet 12. Either synthetic rubber or natural rubber may be used as the elongated stretchable elastic members 15 to 19. In order to bond the two sheet base materials 12S and 12H of the outer sheet 12 and fix the elongated stretchable elastic members 15 to 19 sandwiched therebetween, hot-melt bonding, heat sealing, or ultrasonic bonding may be used in various coating methods. It is not preferable to firmly fix the whole surface of the outer sheet 12, because this impairs the texture of the sheet. Accordingly, it is preferable that after they are combined, only the elastic members 15 to 19 are bonded firmly to these materials, which are not bonded or weakly bonded to each other at rest portions.

More specifically, a plurality of waist edge part stretchable elastic members 17 are fixed between an inside surface of the inside sheet base material 12H and an outside surface of the folded part 12r of the outside sheet base material 12S in the waist edge parts W of the back body part B and of the front body part F, with intervals in the up-down direction so that the members 17 are continued all over in the width direction, and in an stretched state along the width direction with a predetermined elongation rate. Out of the waist edge part stretchable elastic members 17, one or more members 17 disposed to be adjacent to the under waist part U may be overlapped with the inner body 200, or they may be provided at, except for the center part in the width direction overlapped with the inner body 200, the both sides thereof in the width direction. It is preferable that, as the waist edge part stretchable elastic member 17, about 3 to 22 rubber threads having a fineness of about 155 to 1880 dtex, particularly about 310 to 1240 dtex (these ranges are for synthetic rubber, as for natural rubber threads, those having a cross-sectional area of about 0.05 to 1.5 mm$^2$, particularly about 0.1 to 1.0 mm$^2$) are fixed with intervals of 4 to 12 mm in an elongation rate of about 150 to 400%, particularly about 220 to 320%. It is not necessary that all of the waist edge part stretchable elastic members 17 have the same values in the fineness and in the elongation rate and they may have different values in the fineness and elongation rate between an upper part and lower part of the waist edge part W.

In addition, a plurality of waist lower part stretchable elastic members 15 and 19 made of the elongated stretchable elastic members are fixed between an outside surface of the inside sheet base material 12H and an inside surface of the outside sheet base material 12S in the under waist part U of the front body part F and of the back body part B, except for the center part in the width direction overlapped with the inner body 200, at an upper side and both sides in the width direction thereof with intervals in the up-down direction so that the members are continued all over in the width direction, and in a stretched state along the width direction with a predetermined elongation rate.

It is preferable that, as the waist lower part stretchable elastic members 15 and 19, about 5 to 30 rubber threads having a fineness of about 155 to 1880 dtex, particularly about 470 to 1240 dtex (these ranges are for synthetic rubber, as for natural rubber threads, those having a cross-sectional area of about 0.05 to 1.5 mm$^2$, particularly about 0.1 to 1.0 mm$^2$) are fixed with intervals of 1 to 15 mm, particularly 3 to 8 mm in an elongation rate of about 200 to 350%, particularly about 240 to 300%.

In addition, a plurality of intermediate part stretchable elastic members 16 made of the elongated stretchable elastic members are fixed between an outside surface of the inside sheet base material 12H and an inside surface of the outside sheet base material 12S in the intermediate part L of the front body part F and of the back body part B, except for the center part in the width direction overlapped with the inner body 200, at the both sides in the width direction thereof with intervals in the up-down direction so that the members are continued all over in the width direction, and in a stretched state along the width direction with a predetermined elongation rate.

It is preferable that, as the intermediate part stretchable elastic members 16 and 18, about 2 to 10 rubber threads having a thickness of about 155 to 1880 dtex, particularly about 470 to 1240 dtex (these ranges are for synthetic rubber, as for natural rubber threads, those having a cross-sectional area of about 0.05 to 1.5 mm$^2$, particularly about 0.1 to 1.0 mm$^2$) are fixed with intervals of 5 to 40 mm, particularly 5 to 20 mm in an elongation rate of 150 to 300%, particularly 180 to 260%.

When the waist lower part stretchable elastic members and the intermediate part stretchable elastic members 15, 19, 16, and 18 are provided, except for the center part in the width direction overlapped with the inner body 200, at the both sides in the width direction of the center part as shown in the drawings, the inner body 200 is not shrunk in the width direction more than necessary, and thus a bad appearance such as a lumpy appearance does not appear and the absorption property is not reduced. In order to this, in addition to the configuration in which there are the stretchable elastic members only on the both sides in the width direction, a configuration in which there are the stretchable elastic members from one side to the other side in the width direction across the inner body 200, but the stretchable elastic members are cut finely on the center part in the width direction overlapped with the inner body 200, whereby the contraction force is not effected on the center part (which is substantially equal to the configuration in which the stretchable elastic members are not provided there), that is to say, only the both sides in the width direction are set to effect the contraction force. Of course, configuration of the waist lower part stretchable elastic member and the intermediate part stretchable elastic members 15, 19, 16, and 18 is not limited to the examples described above, all of or a part of the waist lower part stretchable elastic members and the intermediate part stretchable elastic members 15, 19, 16, and 18 can be provided from one side to the other side in the width direction across the inner body 200 so that the stretching force is effected over the whole under waist part U in the width direction.

In a case where the elongated stretchable elastic members 15 to 19 provided in each of the parts run across a printed sheet 25 described below, when rubber including titanium oxide is used as the elongated stretchable elastic members 15 to 19, it is preferable to use rubber having a low content of titanium oxide (for example, 2% or less) or rubber having no titanium oxide.

(Post-Treatment Tape)

A post-treatment tape 70 (fixing means) can be provided on the center part in the width direction of the outer surface of the back body part B of the outer sheet 12. The post-treatment tape 70 is used to fix the diaper 100 in a state in which the diaper is rolled up or folded so that the surface sheet 30 is located inside and the front body part F is located inside. In a usual post-treatment tape 70, as shown in FIG. 5, a base portion 71 is fixed to the outer surface of the outer sheet 12 with an adhesive or the like, and the rest of the tape at the leading end-side with respect to the base portion 71 is folded in three (Z-shaped cross-section) or in two, and thus folded portions are removably fixed (temporarily fixed) with an adhesive 72 for temporal fixture. A tab portion 73, which is colored with an opaque color such as white, is provided at the leading end portion of the tape, and the rest of the tape at the base portion-side with respect to the tab portion 73 is transparent or translucent, and thus the design described below can be visually recognized from the outer surface side of the post-treatment tape 70 through the transparent or translucent part in the post-treatment tape 70. Although the specific configuration thereof can be appropriately set, in the structure shown in the drawing, the whole of the tape is formed by connecting a plurality of transparent or translucent base materials in the longitudinal direction and a colored tape 74 is bonded to the tab portion 73.

The diaper 100, when disposed, is rolled up or folded so that the surface sheet 30 is located inside and the front body part F is located inside, then the folded portions of the post-treatment tape 70 are peeled off and extended so as to wrap themselves around the rolled or folded diaper 100 from the back body part B to the opposite outer surface across the waist opening WO for the fixture of the diaper with the adhesive. It is particularly preferable that the post-treatment tape 70 is folded in three, because it can be compact when not used while elongated when used.

Fixing means such as the post-treatment tape 70 may be provided on the front body part F, or on both the back body part B and the front body part F.

(Printed Sheet)

The printed sheet 25, on which the design is given by printing, is provided between the liquid-impermeable back sheet 11 and the outer sheet 12 (including interlayer in the outer sheet 12). The outer sheet 12 may be omitted to expose the printed sheet 25. The printed sheet 25 shown in the drawing has an area smaller than that of the body part on which the sheet is disposed, and the sheets are provided individually on the front body part F and the back body part B. The sheet may be continuously provided as a one sheet from the front body part F to the back body part B through the crotch portion.

The dimensions and the shape of the printed sheet 25 are not particularly limited. In order to obtain sufficient functions, a larger area is preferable, and, for example, the printed sheet 25 has preferably a width of about 50 to 120% of the width of the absorber 56, and the printed sheet 25 has preferably a length of about 15 to 30% of a product full length Y at least on one side of the ventral side and the back side. The shape of the printed sheet 25 is preferably a rectangle as shown in the drawing, in the terms of no generation of trim loss, but the sheet may be in a geometrical shape such as a circle, an ellipse, a triangle, or a hexagon, or it can be shaped so as to contour the design.

As the sheet base material of the printed sheet 25, a plastic film, a non-woven fabric, or paper may be used, and a material having high bulkiness and high air permeability is preferable. When the plastic film is used, it is preferable that the material is moisture-permeable from the viewpoint of prevention of stuffiness. The non-woven fabric and paper are preferable because they are moisture-permeable. When the design printing is performed, it is preferable to use the non-woven fabric having high smoothness and capable of being easily printed, and the paper having high strength and on which an ink is not easily spread. The particularly preferable sheet base material may include crepe paper (thin paper) having a basis weight of about 15 to 35 g/m$^2$ and a thickness of about 0.1 to 0.3 mm, a non-woven fabric having a basis weight of about 10 to 25 g/m$^2$ and a thickness of about 0.1 to 0.3 mm, (in particular a spun-bonded non-woven fabric having a fineness of about 1.0 to 3.0 dtex in the spun-bonded part or an SMS non-woven fabric). When the crepe paper is used, it has preferably a crepe ratio of about 5 to 20%, particularly about 5 to 15%. When the crepe ratio is 20% or more, the amount of the ink fixed is increased, but the ink runs on the paper, and thus it is not suitable for design printing. When the crepe ratio is 5% or less, it is difficult to penetrate the ink, resulting in the small amount of the ink fixed.

(Divided Structure of Outer Sheet)

In the embodiment described above, although the outer sheet 12 continuously covers from the front body part F to the back body part B as one sheet, an outer sheet may be divided into a ventral side outer sheet covering the ventral side of the abdomen of a wearer and a back side outer sheet covering the back side thereof. In this outer sheet, the front end part of the inner body is connected to an inner surface of the central part in the width direction of the ventral side outer sheet with a hot-melt adhesive or the like; the rear end part of the inner body is connected to the inner surface of the central part in the width direction of the back side outer sheet with a hot-melt adhesive or the like, and the ventral side outer sheet and the back side outer sheet are not continued but separated from each other at the crotch portion. The clearance generated by this separation can be from about 150 to 250 mm. In this case, a crotch portion outer sheet also may be fixed on an underside surface of the liquid-impermeable back sheet in the inner body so that it covers the whole underside surface of the inner body or the whole of a part which is located between the ventral side outer sheet and the back side outer sheet so as to be exposed. For such a crotch portion outer sheet, the same materials as used in the aforementioned outer sheet may be used. The crotch portion outer sheet can be determined as the outer sheet in the present invention.

(Side Seal Section)

Figure 9:
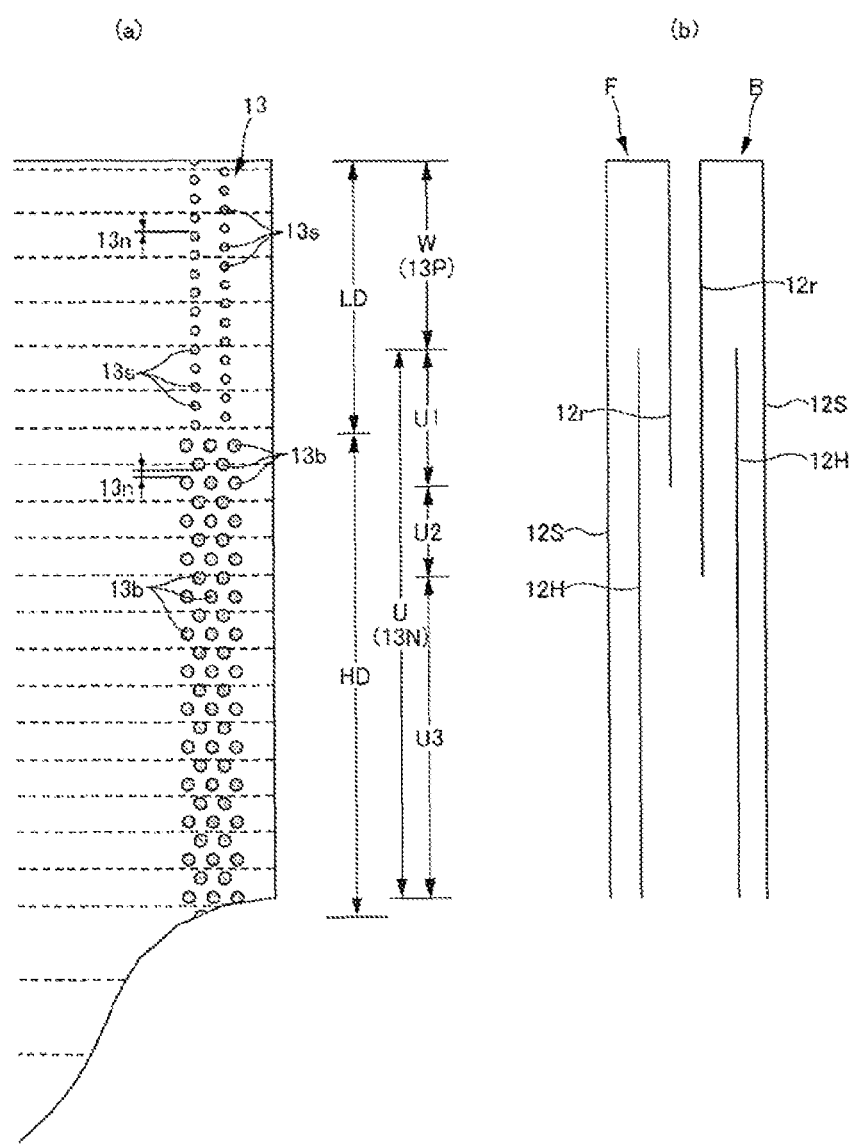
FIG. 9 (a) is an enlarged front view showing a major part of a side seal section and FIG. 9 (b) is a cross-section view thereof.
Figure 10:
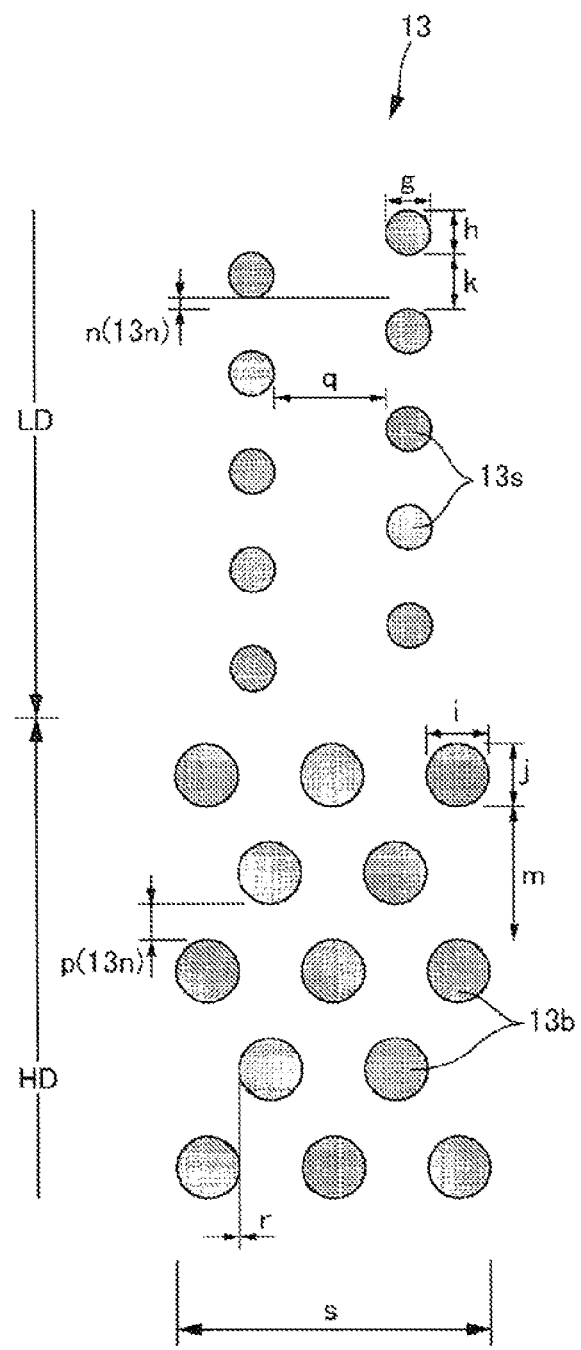
FIG. 10 is an enlarged front view showing a major part of a side seal section.

As shown in FIGS. 9 and 10, in a welding pattern of the side seal section 13 used as a basic pattern, is used a dot pattern, in which a plurality of rows of dot-shaped welded parts 13s and 13b disposed to separate from each other in the vertical direction are arranged in the transverse direction, while non-welded parts 13n disposed all over in the transverse direction are formed on the both sides of each welded part 13s, 13b. In addition, in the side seal section 13, non-densely welded region LD is formed in the vertical direction at least partly while densely welded region HD is formed at least partly in the vertical direction, wherein the degree of density in these welded regions LD and HD is determined so that the area of each welded part 13b in the densely welded region HD is larger than the area of each welded part 13s in the non-densely welded region LD. The area of the welded part 13b in the densely welded region HD may be at least partly smaller than the area of each welded part 13s in the non-densely welded region LD.

The shape of each welded part 13s, 13b is not particularly limited and may be, for example, a polygonal such as triangle, semi-circle, star, or ellipse so long as the shape is dot-shaped, but the circle is preferable as shown in the drawings.

The dimensions and configuration of the dot pattern may be appropriately decided, and the following ranges described below are preferable for the use for babies.

Length g in the transverse direction of each welded part 13s in the non-densely welded region: 0.6 to 3.0 mm (particularly, 0.8 to 1.5 mm)

Length h in the vertical direction of each welded part 13s in the non-densely welded region: 0.6 to 2.0 mm (particularly 0.8 to 1.5 mm)

Length i in the transverse direction of each welded part 13b in the densely welded region: 0.9 to 4.0 mm (particularly 0.9 to 2.0 mm)

Length j in the vertical direction of each welded part 13b in the densely welded region: 0.9 to 2.5 mm (particularly 0.9 to 2.0 mm)

Area ratio between the welded part 13b in the densely welded region and the welded part 13s in the non-densely welded region: 1.5 to 3.5 times (particularly 1.9 to 2.6 times)

The number of rows of the welded parts 13s in the non-densely welded region: 1 to 3 rows, particularly 2 rows The number of rows of the welded parts 13b in the densely welded region: larger than the number of the rows in the non-densely welded region LD, particularly 3 to 6 rows Interval k in the vertical direction between the adjacent welded parts 13s in the row of the welded parts 13s in the non-densely welded region: 0.5 to 5.0 mm (particularly 0.8 to 1.5 mm)

Interval m in the vertical direction between the adjacent welded parts 13b in the row of the welded parts 13b in the densely welded region: 2.0 to 5.0 mm (particularly 2.5 to 3.5 mm)

Length n in the vertical direction of the non-welded part 13n in the non-densely welded region LD: 0.05 to 2.0 mm (particularly 0.1 to 1.0 mm)

Length p in the vertical direction of the non-welded part 13n in the densely welded region HD: 0.05 to 3.0 mm (particularly 0.3 to 1.5 mm)

Interval q in the transverse direction between the rows of the welded parts 13s in the non-densely welded region: +1.0 mm to +4.0 mm Interval r in the transverse direction between the rows of the welded parts 13b in the densely welded region: −1.5 mm to +1.5 mm wherein "−(minus)" means a case where the positions in the transverse direction of the welded parts 13s and 13b in the adjacent rows are overlapped.)

As for the rows of the welded parts 13s and 13b, the positions in the vertical direction of the welded parts 13s and 13b in the adjacent lines of welded parts 13s and 13b may be in line form, but it is preferable that the positions deviate from each other, and it is especially preferable that the welded parts 13s and 13b are alternately arranged in a serpentine pattern, as shown in the drawings.

The non-densely welded region LD is a region improving the ease of tearing. Example of such a region may include a polypropylene region 13P in which only non-woven fabrics of polypropylene or a copolymer thereof are laminated. As described above, the non-woven fabric of the polypropylene or the copolymer thereof is a preferable material, because it is easily stretchable, and a soft texture can be obtained therefrom. When such a polypropylene region 13P is disposed in the side seal section 13, however, the seal strength of this area is several times as much as that of the rest, and it is difficult to apply a force thereto because the material is easily stretched. Accordingly, in the present invention, it is desirable to apply the non-densely welded region LD in such a polypropylene region 13P. This improves the ease of tearing.

Specifically, in the embodiment shown by the drawings, when a PP non-woven fabric is used as the outside sheet base material 12S of the outer sheet 12, the waist edge part W is formed as a polypropylene region 13P in which four sheets of only PP non-woven fabrics are overlapped. As for the ease of tearing of the side seal sections 13, the ease of peeling at the start of tearing is very important. If the diaper had the polypropylene region 13P at the waist edge part W as mentioned above, the seal strength would increase so as to make the user feel difficult to tear off the diaper. Accordingly, it is desirable to apply the non-densely welded region LD in the polypropylene region 13P in the waist edge part W.

The polypropylene region 13P may be provided in other parts than the waist edge part W, but it is desirable that the region is provided only in the waist edge W, as shown in the drawings. In such a case, it is desirable that the whole area on the leg opening LO-side in the waist edge part W is formed of the non-polypropylene region 13N, which is not the polypropylene region 13P, the non-densely welded region LD is set to be provided from the polypropylene region 13P into the non-polypropylene region 13N, and the densely welded region HD is set to be provided on the leg opening LO-side with respect to the non-densely welded region LD so that each welded part 13b has a larger area in the densely welded region HD.

Specifically, in the embodiment shown by the drawings, when the outside sheet base material 12S is formed of a PP non-woven fabric, the side seal section 13 does not have the polypropylene region 13P except for the waist edge part W, and has a first region U1 having the largest number of the non-woven fabrics laminated, a second region U2 having the number of the non-woven fabrics laminated smaller than that in the first region U1, and a third region U3 having the number of the non-woven fabrics laminated smaller than that of the second region U2 in this order in the leg opening LO-side of the waist edge part W. More specifically, each of the front body part F and the back body part B in the first region U1 is a 3-layer lamination of the outside sheet base material 12S, the folded part 12r thereof, and the inside sheet base material 12H, and thus the first region is the total 6-layer lamination; the front body part F of the second region is a 2-layer lamination of the outside sheet base material 12S and the inside sheet base material 12H, and the back body part B thereof is a 3-layer lamination of the outside sheet base material 12S, the folded part 12r thereof, and the inside sheet base material 12H, and thus the second region is the total 5-layer lamination; and each of the front body part F and the back body part B of the third region is a 2-layer lamination of the outside sheet base material 12S and the inside sheet base material 12H, and thus the third region is the total 4-layer lamination.

In the side seal section 13, when the leg opening LO-side portion with respect to the waist edge part W is totally set to be the non-polypropylene region 13N, it is desirable that the non-polypropylene region 13N is set to be the densely welded region HD in order to reduce the variation of the seal strength. Under such condition, when it is intended that a boundary between the non-densely welded region LD and the densely welded region HD is agreed with a boundary between the polypropylene region 13P and the non-polypropylene region 13N, the densely welded region HD might enter the polypropylene region 13P due to manufacturing error, which could likely lead to generation of locally high seal strength. As described before, accordingly, it is desirable that the boundary between the both regions is disposed inside the non-polypropylene region 13N, in particular, on the edge thereof at the polypropylene region 13P-side (in a first region U1 in the embodiment shown by the drawings).

The weld-jointing in the side seal section 13 can be performed by heat-sealing, but it is preferable to perform it by ultrasonic sealing, because the ultrasonic sealing hardly thermally affects a surrounding around the welded part, compared to the heat sealing, and the finished material in the side seal section 13 is easily stretchable and is soft. However, the ultrasonic sealing makes the user feel more difficult to tear off the diaper, when compared to the heat sealing in terms of the same seal pattern, because of the easy stretchability of the material. The non-densely welded region LD, accordingly, is preferably functioned in using the ultrasonic sealing. The ultrasonic sealing is not particularly limited, and any known method can be adopted. Specifically, the frequency in the ultrasonic sealing can be appropriately adopted by selecting from the usually adopted frequencies of 15 kHz, 20 kHz, 30 kHz, 40 kHz, 50 kHz, 70 kHz, and the like. The clearance between a horn and an anvil in the ultrasonic sealing can be arbitrarily adjusted depending on the thickness of the target to be sealed, and the pressure pressurized by the anvil and horn can be set at about 1,000 to 2,500 N.

In general, in order to tear off the side seal sections 13 of the underpants-type disposable diaper, hands are put into the front body part F-side and the back body part B-side from the waist opening WO, the front body part F-side and the back body part B-side of the side seal sections 13 are grabbed by the hands, and the front body part F and the back body part B are pulled so as to separate from each other as indicated by arrows in FIG. 8, whereby welded parts 13s, 13b forming the side seal sections 13 are torn sequentially from the waist side. In this occasion, the seal strength depends on the total area of the welded parts, which are removed at once, and thus the seal strength is high in the densely welded region HD while the seal strength is weak in the non-densely welded region LD. Both the sufficient strength during the use of the diaper and the ease of tearing can be achieved, accordingly, by providing the densely welded region HD and the non-densely welded region LD at appropriate sites depending on the site in the side seal section 13.

Particularly, the side seal sections 13 are formed in a dot pattern having the non-welded parts 13n, disposed all over in the transverse direction, on both sides of each welded part 13s, 13b in the vertical direction, which inhibits the fiber waste of the non-woven fabric from sticking in gaps between protrusions for forming the welded parts in a sealing device, and the stuck fiber waste can be easily removed. In manufacturing of the underpants-type disposable diaper, the side seal sections 13 are formed while the diaper is moved in the transverse direction; as a result, even if the fiber waste is generated, it is discharged through depression grooves (between the protrusions for forming the welded parts) for forming the non-welded parts 13n in the sealing device, which prevents the fiber waste from accumulating between the protrusions for forming the welded parts. Specifically, the staying time of the fiber waste is substantially the same as that in the conventional general horizontal stripe pattern. Even if the fiber waste has accumulated between the protrusions for forming the welded parts after a long period of time elapses, it can be easily removed only by brushing in a flow direction of the line, because the grooves between the protrusions run continuously in the flow direction of the line.

EXAMPLES

Figure 11:
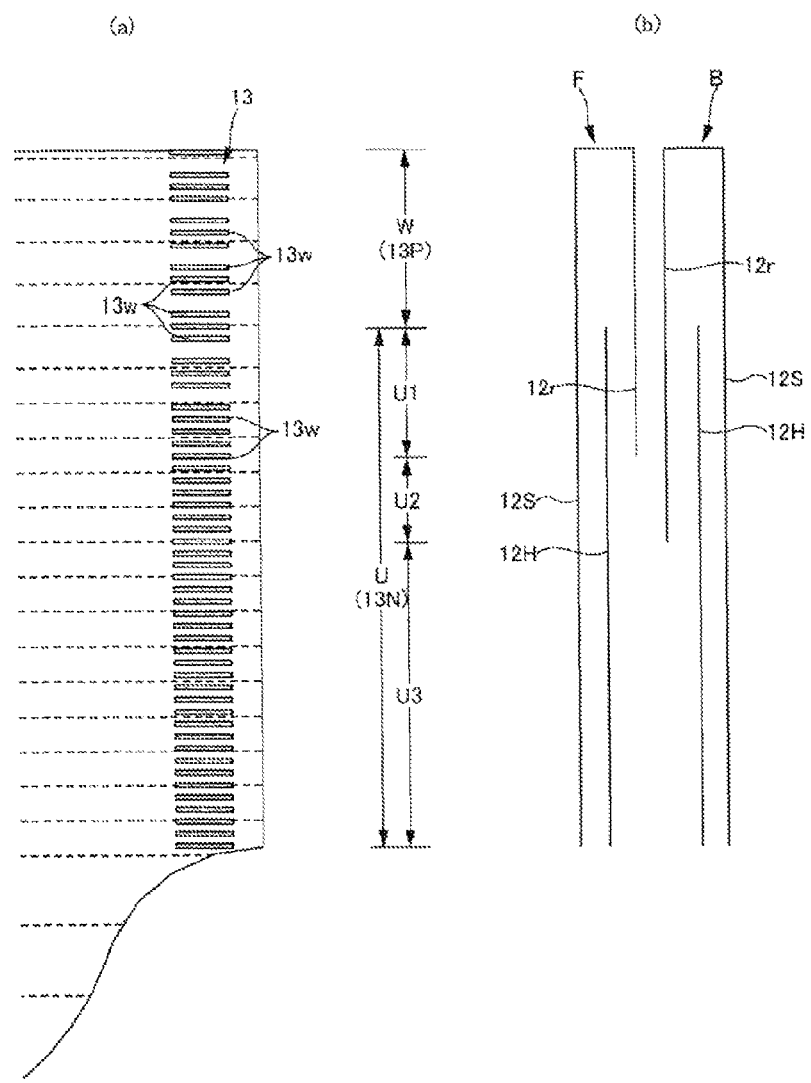
FIG. 11 (a) is an enlarged front view showing a major part of a side seal section, and FIG. 11 (b) is a cross-section view thereof.
Figure 12:
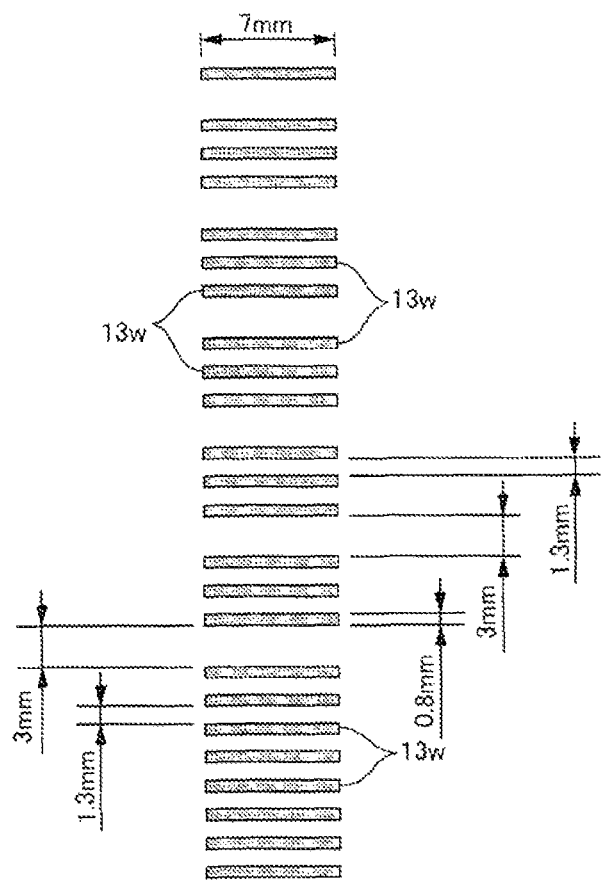
FIG. 12 is an enlarged front view showing a major part of a side seal section.

An underpants-type disposable diaper for test including a side seal section 13 of the present invention, shown in FIGS. 9 and 10, and an underpants-type disposable diaper for test including a side seal section 13 (reference number 13W denotes a welded part) for comparison, shown in FIGS. 11 and 12 were produced, and the following tests and evaluations were performed. The dimensions of each member of the side seal section 13 according to the present invention were as follows:

Shape of welded part 13s, 13b: circle
Diameter of a welded part 13s in a non-densely welded region (length g in the transverse direction and length h in the vertical direction): 1.0 mm
Diameter of the welded part 13b in a densely welded region (length i in the transverse direction and length j in the vertical direction): 1.4 mm
Area ratio between the welded part 13b in the densely welded region and the welded part 13s in the non-densely welded region: 1.96 times
The number of rows of the welded parts 13s in the non-densely welded region: 2 rows
The number of rows of the welded parts 13b in the densely welded region: 5 rows
Interval k in the vertical direction between the adjacent welded parts 13s in the rows of the welded parts 13s in the non-densely welded region: 1.2 mm
Interval m in the vertical direction between the adjacent welded parts 13b in the rows of welded parts 13b in the densely welded region: 3.0 mm
Length n in the vertical direction of the non-welded part 13n in the non-densely welded region LD: 0.1 mm
Length p in the vertical direction of the non-welded part 13n in the densely welded region HD: 0.8 mm
Interval q in the transverse direction between the rows of the welded part 13s in the non-densely welded region: +2.5 mm
Interval r in the transverse direction between the rows of the welded parts 13b in the densely welded region: 0 mm
Length s in the transverse direction in the side seal section 13 (the maximum width of the welded part): 7 mm In the all examples, the side seal sections 13 were weld-jointed by ultrasonic sealing (Frequency: 20 kHz, Clearance (interval) between an anvil and a horn: 0.5 mm and Pressure pressurized by the anvil and horn: 1,000 to 2,000 N).

<Peel Strength Test>

From a part on the left side and a part on the right side with respect to the inner body 200 in the underpants-type disposable diaper, a part with a width of 25 mm from the edge of a waist opening WO toward a leg opening LO (hereinafter which may sometimes to referred to as an "upper part") and a part with a width of 25 mm from the upper end of the leg opening LO toward the waist opening WO (hereinafter which may sometimes referred to as a "lower part") were cut from the diaper as samples. The front body part F-side and the back body part B-side of the sample were grabbed by both chucks in a tension tester (for example, AOUTGRAPHAGS-G100N manufactured by SHIMADZU Corporation) so that a direction orthogonal to the side seal section 13 of the sample (a circumferential direction of the diaper) was a tensile direction. The tensile test was performed at room temperature under the condition where a distance between the chucks is 50 mm and a tensile speed is 500 mm/minute, whereby a strength at breakage was measured as a seal strength. The measurement was performed for twenty diapers, and an average value and 3σ and the like were calculated.

The test results are shown in Table 1. In Table 1, gsm means g/m$^2$; PP means polypropylene; a PP copolymer means a copolymer in which ethylene was used for copolymerization; a PE/PP bi-component means a core-sheath fiber having polyethylene (PE) as a sheath and polypropylene (PP) as a core component; an SS non-woven fabric and an SSS non-fabric mean respectively a laminated non-woven fabric of two spun-bonded layers and a laminated non-woven fabric of three spun-bonded layers; and an SSMS non-woven fabric means a laminated non-woven fabric in which one melt-blown layer is put between two spun-bonded layers and one spun-bonded layer. Meanwhile, the outside sheet base material of Sample No. 3 and the outside sheet base material of Sample No. 4 were manufactured by different manufacturers.

As shown in Table 1, in each of Samples No. 2 to No. 6 according to the present invention, the seal strength of the upper part was reduced compared to Sample No. 1 of Comparative Example, and the variation between the upper part and the lower part was little (3σ is small).

TABLE 1

| No. | Outside sheet base material | Position of side seal section | | 1 | 2 | 3 | 4 | 5 | 6 | 7 | 8 | 9 | 10 | 11 | 12 | 13 |
|---|---|---|---|---|---|---|---|---|---|---|---|---|---|---|---|---|
| 1 | Outside: PP<br>SS non-woven fabric: 18 gsm<br>Inside: PE/PP bi-component<br>SS non-woven fabric: 18 gsm<br>Side seal pattern: Comparative Example | Right | Upper part | 2.8 | 3.1 | 2.5 | 2.4 | 2.6 | 2.9 | 2.4 | 3.0 | 2.9 | 2.5 | 3.4 | 2.5 | 2.4 |
| | | | Lower part | 1.3 | 1.5 | 1.1 | 1.5 | 1.3 | 1.6 | 1.1 | 1.1 | 1.1 | 1.3 | 1.7 | 1.6 | 1.4 |
| | | Left | Upper part | 2.7 | 3.1 | 3.2 | 3.0 | 3.1 | 2.7 | 2.3 | 3.0 | 2.5 | 2.6 | 2.2 | 3.3 | 2.5 |
| | | | Lower part | 1.7 | 1.7 | 1.6 | 1.5 | 1.8 | 2.2 | 1.0 | 1.1 | 1.2 | 1.0 | 2.2 | 2.0 | 2.0 |
| 2 | Outside: PP<br>SS non-woven fabric: 18 gsm<br>Inside: PE/PP bi-component<br>SS non-woven fabric: 18 gsm<br>Side seal pattern: Present invention | Right | Upper part | 1.2 | 1.2 | 1.3 | 1.2 | 1.4 | 1.6 | 1.6 | 1.3 | 1.6 | 1.5 | 1.8 | 1.3 | 1.5 |
| | | | Lower part | 1.5 | 1.8 | 1.8 | 1.7 | 1.7 | 2.0 | 1.4 | 2.2 | 1.7 | 2.0 | 1.6 | 2.1 | 1.2 |
| | | Left | Upper part | 1.5 | 1.5 | 1.3 | 1.6 | 1.5 | 1.4 | 1.7 | 1.6 | 1.4 | 1.5 | 1.2 | 1.5 | 1.3 |
| | | | Lower part | 1.7 | 2.1 | 1.5 | 1.9 | 1.4 | 1.7 | 2.0 | 1.9 | 1.5 | 1.7 | 1.9 | 1.4 | 1.7 |
| 3 | Outside: PP copolymer<br>SSS non-woven fabric: 17 gsm<br>Inside: PE/PP bi-component<br>SS non-woven fabric: 18 gsm<br>Side seal pattern: Present invention | Right | Upper part | 1.4 | 1.8 | 1.2 | 1.4 | 1.7 | 1.9 | 1.4 | 1.5 | 1.7 | 1.5 | 1.9 | 1.1 | 1.4 |
| | | | Lower part | 1.4 | 1.4 | 1.5 | 1.9 | 1.0 | 1.2 | 1.3 | 1.4 | 1.1 | 0.8 | 1.1 | 1.0 | 1.2 |
| | | Left | Upper part | 1.7 | 1.8 | 1.7 | 1.5 | 2.2 | 1.5 | 1.5 | 1.6 | 1.8 | 1.7 | 1.8 | 1.7 | 1.7 |
| | | | Lower part | 1.5 | 1.9 | 1.8 | 2.0 | 1.7 | 1.1 | 1.4 | 1.0 | 1.5 | 1.5 | 0.9 | 1.3 | 1.8 |
| 4 | Outside: PP copolymer<br>SSS non-woven fabric: 17 gsm<br>Inside: PE/PP bi-component<br>SS non-woven fabric: 18 gsm<br>Side seal pattern: Present invention | Right | Upper part | 1.5 | 1.4 | 1.8 | 1.7 | 1.2 | 1.9 | 1.9 | 1.9 | 1.8 | 1.5 | 2.1 | 1.7 | 1.8 |
| | | | Lower part | 1.5 | 1.6 | 1.7 | 1.6 | 1.6 | 1.8 | 1.7 | 1.6 | 1.4 | 1.5 | 1.8 | 1.7 | 1.5 |
| | | Left | Upper part | 1.7 | 1.3 | 1.7 | 1.2 | 1.7 | 1.6 | 1.8 | 1.9 | 1.4 | 1.5 | 1.5 | 1.6 | 1.6 |
| | | | Lower part | 1.6 | 1.5 | 1.7 | 1.3 | 1.4 | 1.6 | 1.5 | 1.7 | 1.4 | 1.6 | 1.1 | 1.7 | 1.6 |
| 5 | Outside: PP copolymer<br>SSMS non-woven fabric: 18 gsm<br>Inside: PE/PP bi-component<br>SS non-woven fabric: 18 gsm<br>Side seal pattern: Present invention | Right | Upper part | 1.4 | 1.4 | 1.4 | 1.6 | 1.6 | 1.6 | 1.5 | 1.4 | 1.8 | 1.7 | 1.7 | 1.6 | 1.5 |
| | | | Lower part | 1.9 | 1.7 | 1.4 | 1.8 | 1.3 | 1.4 | 1.4 | 1.2 | 1.6 | 1.5 | 1.5 | 1.5 | 1.7 |
| | | Left | Upper part | 1.3 | 1.5 | 1.3 | 1.4 | 1.1 | 1.1 | 1.3 | 1.5 | 1.6 | 1.6 | 1.6 | 1.2 | 1.2 |
| | | | Lower part | 1.6 | 1.5 | 1.4 | 1.4 | 1.5 | 1.5 | 1.4 | 1.5 | 1.8 | 1.5 | 1.7 | 1.6 | 1.9 |
| 6 | Outside: PP copolymer<br>SSMS non-woven fabric: 18 gsm<br>Inside: PE/PP bi-component<br>SS non-woven fabric: 20 gsm<br>Side seal pattern: Present invention | Right | Upper part | 1.8 | 1.5 | 1.5 | 1.5 | 1.6 | 1.5 | 1.6 | 1.6 | 1.5 | 1.5 | 1.6 | 1.6 | 1.5 |
| | | | Lower part | 1.2 | 1.5 | 1.2 | 1.3 | 1.8 | 1.5 | 1.3 | 1.4 | 1.3 | 1.4 | 1.4 | 1.4 | 1.3 |
| | | Left | Upper part | 1.4 | 1.4 | 1.5 | 1.5 | 1.6 | 1.4 | 1.5 | 1.3 | 1.5 | 1.5 | 1.4 | 1.5 | 1.4 |
| | | | Lower part | 1.4 | 1.5 | 1.4 | 1.4 | 1.2 | 1.5 | 1.2 | 1.2 | 1.6 | 1.1 | 1.3 | 1.4 | 1.5 |

| No. | Outside sheet base material | Position of side seal section | | 14 | 15 | 16 | 17 | 18 | 19 | 20 | Average | σ | 3σ |
|---|---|---|---|---|---|---|---|---|---|---|---|---|---|
| 1 | Outside: PP<br>SS non-woven fabric: 18 gsm<br>Inside: PE/PP bi-component<br>SS non-woven fabric: 18 gsm<br>Side seal pattern: Comparative Example | Right | Upper part | 2.0 | 2.3 | 2.7 | 2.9 | 3.4 | 2.9 | 2.9 | 2.7 | 0.71 | 2.13 |
| | | | Lower part | 1.7 | 1.9 | 1.5 | 1.6 | 1.4 | 1.3 | 1.6 | 1.4 | | |
| | | Left | Upper part | 2.6 | 2.0 | 2.7 | 2.7 | 3.1 | 2.5 | 2.8 | 2.7 | | |
| | | | Lower part | 1.1 | 1.7 | 1.4 | 1.0 | 1.5 | 1.9 | 1.2 | 1.5 | | |
| 2 | Outside: PP<br>SS non-woven fabric: 18 gsm<br>Inside: PE/PP bi-component<br>SS non-woven fabric: 18 gsm<br>Side seal pattern: Present invention | Right | Upper part | 1.3 | 1.0 | 1.7 | 1.2 | 1.5 | 1.5 | 1.6 | 1.3 | 0.25 | 0.74 |
| | | | Lower part | 1.5 | 2.1 | 1.9 | 1.6 | 2.0 | 1.8 | 2.0 | 1.7 | | |
| | | Left | Upper part | 1.2 | 1.7 | 1.5 | 1.4 | 1.5 | 1.3 | 1.6 | 1.5 | | |
| | | | Lower part | 1.6 | 1.5 | 1.7 | 1.8 | 1.9 | 2.0 | 1.4 | 1.7 | | |
| 3 | Outside: PP copolymer<br>SSS non-woven fabric: 17 gsm<br>Inside: PE/PP bi-component<br>SS non-woven fabric: 18 gsm<br>Side seal pattern: Present invention | Right | Upper part | 1.7 | 1.4 | 1.8 | 1.5 | 1.4 | 1.6 | 1.5 | 1.5 | 0.29 | 0.86 |
| | | | Lower part | 1.0 | 0.9 | 0.9 | 0.8 | 1.4 | 1.3 | 0.9 | 1.4 | | |
| | | Left | Upper part | 1.7 | 1.8 | 1.8 | 1.5 | 1.6 | 1.6 | 1.6 | 1.8 | | |
| | | | Lower part | 1.0 | 1.7 | 1.7 | 1.4 | 1.8 | 1.2 | 1.2 | 1.8 | | |

TABLE 1-continued

| | | | | | | | | | | | | | |
|---|---|---|---|---|---|---|---|---|---|---|---|---|---|
| 4 | Outside: PP copolymer SSS non-woven fabric: 17 gsm Inside: PE/PP bi-component SS non-woven fabric: 18 gsm Side seal pattern: Present invention | Right | Upper part | 1.7 | 1.7 | 1.6 | 1.5 | 1.9 | 1.7 | 1.7 | 1.5 | 0.18 | 0.54 |
| | | | Lower part | 1.7 | 1.4 | 1.4 | 1.3 | 1.4 | 1.4 | 1.5 | 1.6 | | |
| | | Left | Upper part | 1.4 | 2.0 | 1.3 | 1.7 | 1.4 | 1.6 | 1.5 | 1.5 | | |
| | | | Lower part | 1.6 | 1.8 | 1.6 | 1.1 | 1.8 | 1.6 | 1.5 | 1.5 | | |
| 5 | Outside: PP copolymer SSMS non-woven fabric: 18 gsm Inside: PE/PP bi-component SS non-woven fabric: 18 gsm Side seal pattern: Present invention | Right | Upper part | 1.6 | 1.5 | 1.6 | 1.3 | 1.3 | 1.4 | 1.3 | 1.5 | 0.19 | 0.56 |
| | | | Lower part | 1.5 | 1.5 | 1.7 | 1.5 | 1.5 | 1.4 | 1.5 | 1.6 | | |
| | | Left | Upper part | 1.4 | 1.5 | 1.2 | 1.3 | 1.7 | 1.4 | 1.5 | 1.3 | | |
| | | | Lower part | 1.8 | 1.8 | 1.5 | 1.7 | 1.4 | 1.8 | 1.8 | 1.5 | | |
| 6 | Outside: PP copolymer SSMS non-woven fabric: 18 gsm Inside: PE/PP bi-component SS non-woven fabric: 20 gsm Side seal pattern: Present invention | Right | Upper part | 1.5 | 1.4 | 1.3 | 1.3 | 1.8 | 1.4 | 1.5 | 1.6 | 0.17 | 0.50 |
| | | | Lower part | 1.4 | 1.6 | 1.4 | 1.5 | 1.4 | 1.4 | 1.4 | 1.4 | | |
| | | Left | Upper part | 1.4 | 1.6 | 1.4 | 1.6 | 1.4 | 1.4 | 1.5 | 1.5 | | |
| | | | Lower part | 1.5 | 1.4 | 1.3 | 1.4 | 1.5 | 1.6 | 1.7 | 1.4 | | |

<Sensory Evaluation>

Sensory evaluation in tearing of the side seal section was carried out by twenty testers on a scale of 1 to 5 (5: It is very easy to tear the section. 4: It is slightly easy to tear the section. 3: Normal. 2: It is slightly difficult to tear the section. 1: It is very difficult to tear the section). The test results are shown in Table 2. The results show that Samples Nos. 2 to 6 according to the present invention were outstandingly easily torn compared to Sample No. 1 of Comparative Example.

TABLE 2

| No. | 1 | 2 | 3 | 4 | 5 | 6 | 7 | 8 | 9 | 10 | 11 | 12 | 13 | 14 | 15 | 16 | 17 | 18 | 19 | 20 | Average |
|---|---|---|---|---|---|---|---|---|---|---|---|---|---|---|---|---|---|---|---|---|---|
| 1 | 1.0 | 1.0 | 1.0 | 2.0 | 1.0 | 2.0 | 2.0 | 2.0 | 1.0 | 2.0 | 2.0 | 2.0 | 2.0 | 2.0 | 1.0 | 1.0 | 2.0 | 2.0 | 1.0 | 1.0 | 1.6 |
| 2 | 5.0 | 5.0 | 4.0 | 5.0 | 5.0 | 5.0 | 4.0 | 4.0 | 5.0 | 4.0 | 5.0 | 4.0 | 4.0 | 4.5 | 5.0 | 4.0 | 4.0 | 4.0 | 4.0 | 4.0 | 4.4 |
| 3 | 4.5 | 4.0 | 4.0 | 4.0 | 4.0 | 4.0 | 5.0 | 3.0 | 4.0 | 5.0 | 5.0 | 4.0 | 4.0 | 3.0 | 4.5 | 4.0 | 4.5 | 4.0 | 3.0 | 4.0 | 4.1 |
| 4 | 4.5 | 4.0 | 5.0 | 5.0 | 5.0 | 4.0 | 5.0 | 4.0 | 5.0 | 4.0 | 5.0 | 4.0 | 5.0 | 5.0 | 4.5 | 5.0 | 4.0 | 3.0 | 4.0 | 5.0 | 4.5 |
| 5 | 5.0 | 5.0 | 5.0 | 5.0 | 5.0 | 5.0 | 5.0 | 5.0 | 5.0 | 5.0 | 5.0 | 4.0 | 4.0 | 4.5 | 3.0 | 5.0 | 5.0 | 4.0 | 4.0 | 5.0 | 4.7 |
| 6 | 5.0 | 5.0 | 5.0 | 5.0 | 5.0 | 5.0 | 5.0 | 5.0 | 4.0 | 4.0 | 5.0 | 5.0 | 5.0 | 4.5 | 5.0 | 4.0 | 4.0 | 4.0 | 4.0 | 5.0 | 4.7 |

INDUSTRIAL APPLICABILITY

The present invention can be utilized in underpants-type disposable diaper having a side seal section.

REFERENCE SIGNS LIST

11 . . . Liquid-impermeable back sheet, 12 . . . Outer sheet, 12r . . . Folded part, 12S . . . Outside sheet base material, 12H . . . Inside sheet base material, 13 . . . Side seal section, 13s, 13b . . . Welded part, 13s . . . Welded part of non-densely welded region, 13b . . . Welded part of densely welded region, 13n . . . Non-welded part, 13P . . . Polypropylene region, 13N inside . . . Non-polypropylene region, 25 . . . Printed sheet, 200 . . . Inner body, 30 . . . Top sheet, 40 . . . Interlayer sheet, 50 . . . Absorbent element, 56 . . . Absorber, 58 . . . Wrapping sheet, 60 . . . Three dimensional gather, 62 . . . Gather sheet, F . . . Front body part, B . . . Back body part, W . . . Waist edge part, WO . . . Waist opening, LO . . . Leg opening, LD . . . Non-densely welded region, HD . . . Densely welded region.

The invention claimed is:

1. An underpants-type disposable diaper, in which a front body part and a back body part are each weld-jointed together on both sides to form side seal sections, thereby forming a waist opening and a right-left pair of leg openings, wherein:

at least an outer surface of the side seal section is formed of a non-woven fabric;

the side seal section is formed in a dot pattern in which a plurality of rows of dot-shaped welded parts, disposed with intervals in a vertical direction, are disposed in a transverse direction, and non-welded parts, disposed all over in the transverse direction, are disposed on both sides of each welded part in the vertical direction;

the side seal section is set to have a non-densely welded region closer to the waist opening than a densely welded region the non-densely welded region being vertically separated from the densely welded region; and each welded part in the densely welded region is at least partly larger in area than each welded part in the non-densely welded region;

the side seal section has a polypropylene region where only non-woven fabrics of polypropylene or a copolymer thereof are laminated and a non-polypropylene region;

the non-polypropylene region having first, second and third regions, the first region being immediately below the polypropylene region, the second region being immediately below the first region and the third region being immediately below the second region;

the first region having a first number of non-woven fabrics laminated, the second region having a second number, which is smaller than the first number, of non-woven fabrics laminated, and the third region having a third number, smaller than the second number, of non-woven fabrics laminated;

whereby the front body part is more easily separated from the back body at the waist opening.

2. The underpants-type disposable diaper according to claim 1, wherein in the side seal section, a waist edge part is in the polypropylene region, and leg opening-side portion with respect to the waist edge part is totally in the non-polypropylene region, and the non-densely welded region is provided from the polypropylene region into the first region of the non-polypropylene region, and the densely welded region is provided on the leg opening-side with respect to the non-densely welded region.

3. The underpants-type disposable diaper according to claim 1, wherein each welded part in the side seal section has the shape of a circle having a diameter of 0.7 to 2.0 mm, each welded part in the densely welded region has an area being 1.5 to 3.5 times as large as each welded part in the non-densely welded region, the number of rows of the welded parts arranged in the non-densely welded region is two, the number of rows of the welded parts arranged in the densely welded region is more than the number of the rows in the non-densely welded region, the non-welded part in the non-densely welded region has a length of 0.05 to 2.0 mm in the vertical direction, and the non-welded part in the densely welded region has a length of 0.05 to 3.0 mm in the vertical direction.

4. The underpants-type disposable diaper according to claim 1, wherein weld-jointing is performed by ultrasonic sealing.

5. The underpants-type disposable diaper according to claim 2, wherein the densely welded region is provided in part of the first region, all of the second region and all of the third region.

* * * * *